(12) United States Patent
Feng et al.

(10) Patent No.: US 11,835,605 B2
(45) Date of Patent: Dec. 5, 2023

(54) METHODS AND SYSTEMS FOR A FLOATING CABLE TRAP

(71) Applicant: GE Precision Healthcare LLC, Wauwatosa, WI (US)

(72) Inventors: Limin Feng, Solon, OH (US); Aleksey Zemskov, Solon, OH (US)

(73) Assignee: GE PRECISION HEALTHCARE LLC, Wauwatosa, WI (US)

( * ) Notice: Subject to any disclaimer, the term of this patent is extended or adjusted under 35 U.S.C. 154(b) by 204 days.

(21) Appl. No.: 17/646,242

(22) Filed: Dec. 28, 2021

(65) Prior Publication Data

US 2022/0155389 A1    May 19, 2022

Related U.S. Application Data

(63) Continuation-in-part of application No. 16/578,197, filed on Sep. 20, 2019, now Pat. No. 11,243,282.

(51) Int. Cl.
| | |
|---|---|
| *G01R 33/36* | (2006.01) |
| *H01F 27/24* | (2006.01) |
| *H01F 27/28* | (2006.01) |
| *H01F 27/30* | (2006.01) |
| *H05K 1/02* | (2006.01) |
| *H01F 27/40* | (2006.01) |

(52) U.S. Cl.
CPC ..... *G01R 33/3628* (2013.01); *G01R 33/3685* (2013.01); *H01F 27/24* (2013.01); *H01F 27/2823* (2013.01); *H01F 27/306* (2013.01); *H01F 27/40* (2013.01); *H05K 1/0243* (2013.01); *H05K 2201/1003* (2013.01); *H05K 2201/10015* (2013.01)

(58) Field of Classification Search
CPC . G01R 33/3628; G01R 33/3685; H01F 27/24; H01F 27/2823; H01F 27/306; H01F 27/40; H01F 27/289; H01F 2005/022; H01F 5/02; H01F 27/325; H05K 1/0243; H05K 2201/10015; H05K 2201/1003; H05K 1/165; H05K 2201/086; H05K 1/18; A61B 5/055
See application file for complete search history.

(56) References Cited

U.S. PATENT DOCUMENTS

| | | | |
|---|---|---|---|
| 10,185,002 B2 | 1/2019 | Stormont et al. | |
| 10,209,328 B2 | 2/2019 | Taracila et al. | |
| 2017/0343627 A1 | 11/2017 | Taracila et al. | |
| 2017/0343628 A1* | 11/2017 | Taracila | G01R 33/307 |
| 2019/0265316 A1 | 8/2019 | Wynn et al. | |

FOREIGN PATENT DOCUMENTS

WO    2010003215 A1    1/2010

\* cited by examiner

*Primary Examiner* — G. M. A Hyder
(74) *Attorney, Agent, or Firm* — McCoy Russell LLP

(57) ABSTRACT

Various methods and systems are provided for a current trap. In one example, the current trap has a flat core made of a nonconductive material, a coiled wire having a plurality of turns winding around the flat spiral core, and one or more tuning capacitors physically attached to the flat core and electrically connected to the coiled wire to form a resonant circuit with the coiled wire.

20 Claims, 13 Drawing Sheets

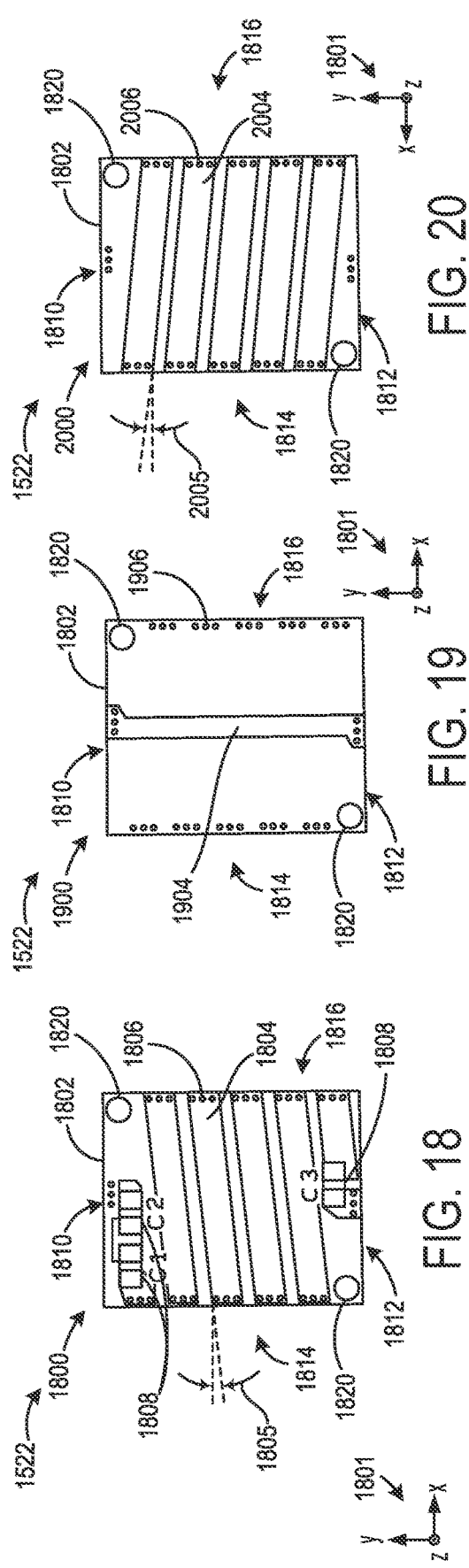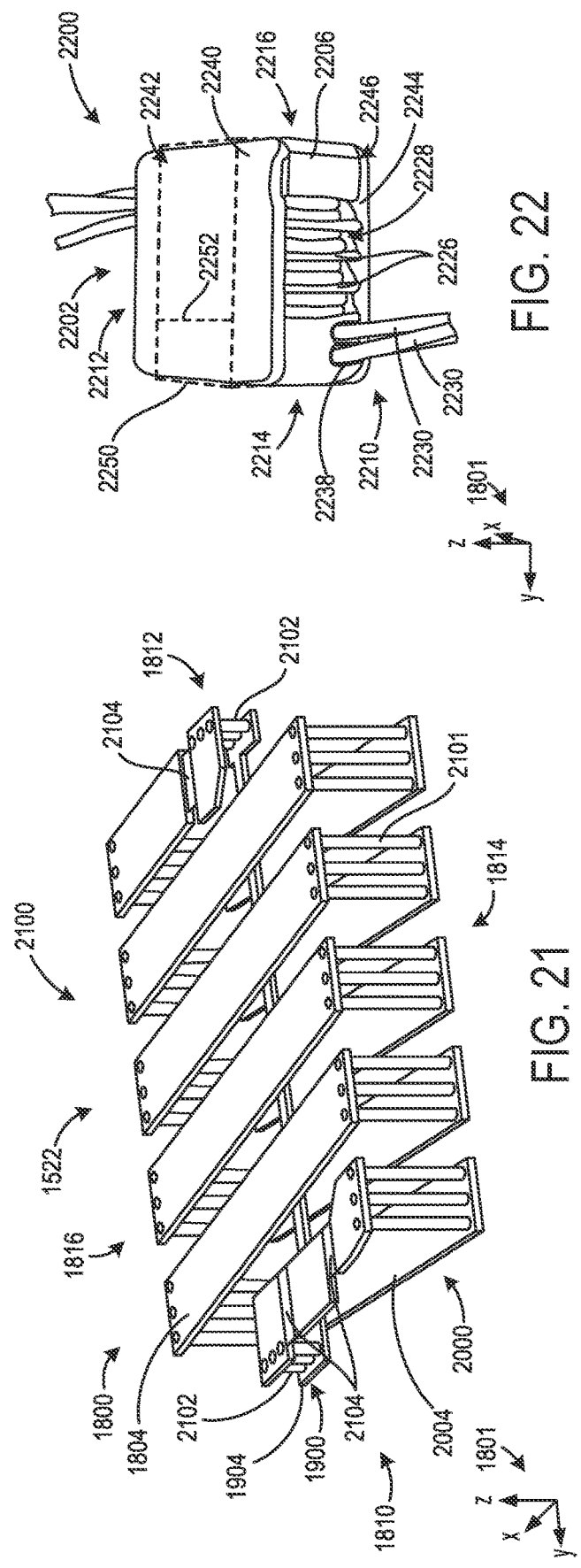

METHODS AND SYSTEMS FOR A FLOATING CABLE TRAP

CROSS-REFERENCE TO RELATED APPLICATIONS

The present application is a continuation-in-part of U.S. Non-Provisional patent application Ser. No. 16/578,197, entitled "METHODS AND SYSTEMS FOR A FLOATING CABLE TRAP", and filed on Sep. 20, 2019. The entire contents of the above-listed application are hereby incorporated by reference for all purposes.

FIELD

Embodiments of the subject matter disclosed herein relate to magnetic resonance imaging, and more particularly, to a current trap for a magnetic resonance imaging system.

BACKGROUND

Magnetic resonance imaging (MRI) is a medical imaging modality that can create images of the inside of a human body without using x-rays or other ionizing radiation. MRI systems include a superconducting magnet to create a strong, uniform, static magnetic field Bo. Exposure of a human body, or part of a human body, to the magnetic field Bo, induces polarization of hydrogen nuclear spin in tissue water. The nuclei are excited by a radio frequency signal and upon relaxation to a rest energy state, energy is released as an RF signal which may be transformed into an image.

An MRI system utilizes RF coils to transmit RF excitations and/or receive MR signals. Shielded coil-interfacing cables may be used to transmit signals between the RF coils and other aspects of a processing system of the MRI system. For example, the coil-interfacing cables may transmit signals to control the RF coils and/or to receive signals from the RF coils. The coil-interfacing cables may be subjected to electro-magnetic fields and as a result, transmitter-driven common mode currents may adversely affect coil tuning, coil-to-coil coupling in phased array coils, inhomogeneity in generated images, and/or unpredictable heating of components.

Common mode traps, or baluns, providing high common mode impedances, may be used to mitigate the effect of transmitter-driven currents. Conventionally, grounded baluns may be coupled to the coil-interfacing cables to block the induced currents. However, coupling of the baluns to the coil-interfacing cables may demand a complex soldering process. The soldering process may expose conductors in the coil-interfacing cables to high temperatures, leading to degradation of the conductors.

BRIEF DESCRIPTION

In one embodiment, a current trap includes a flat core made of a nonconductive material, a coiled wire having a plurality of turns wound around the flat spiral core, and one or more tuning capacitors physically attached to the flat core and electrically connected to the coiled wire to form a resonant circuit with the coiled wire. In this way, soldering of the current trap assembly to coil-interfacing cables is not demanded and the current trap assembly may be located anywhere along the cables.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present disclosure will be better understood from reading the following description of non-limiting embodiments, with reference to the attached drawings, wherein below:

FIG. 18 shows a view of a top layer of a printed circuit board (PCB) for use in the current trap assembly of FIG. 15.

FIG. 19 shows a view of a middle layer of a printed circuit board (PCB) for use in the current trap assembly of FIG. 15.

FIG. 20 shows a view of a bottom layer of a printed circuit board (PCB) for use in the current trap assembly of FIG. 15.

FIG. 21 illustrates exemplary electrical connections between conductive traces formed in the layers of the PCB depicted in FIGS. 18-20.

FIG. 22 is a perspective view of a shielded current trap according to another exemplary embodiment of the disclosure.

FIGS. 3-10, 15-20, and 22 are drawn approximately to scale.

DETAILED DESCRIPTION

Figure 2:
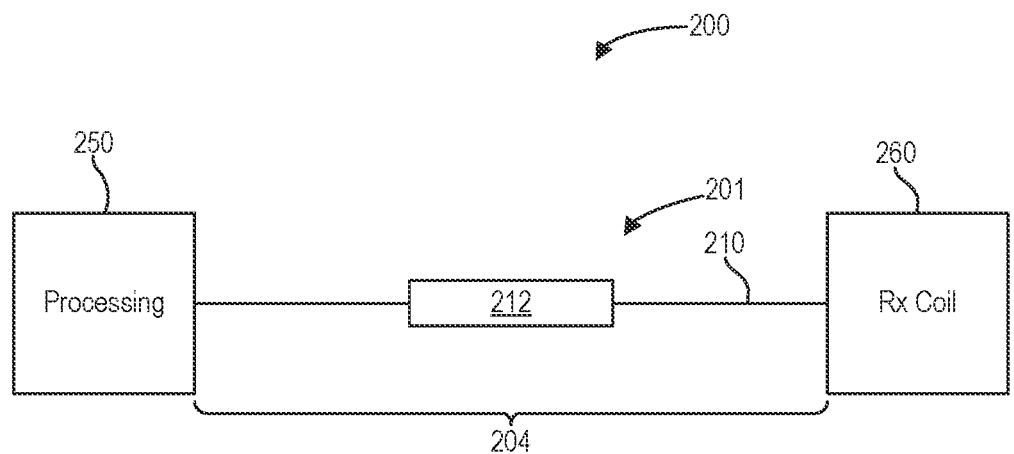
FIG. 2 is a block schematic diagram of a current trap assembly which may be implemented in the MRI system according to an exemplary embodiment of the disclosure.
Figure 3:
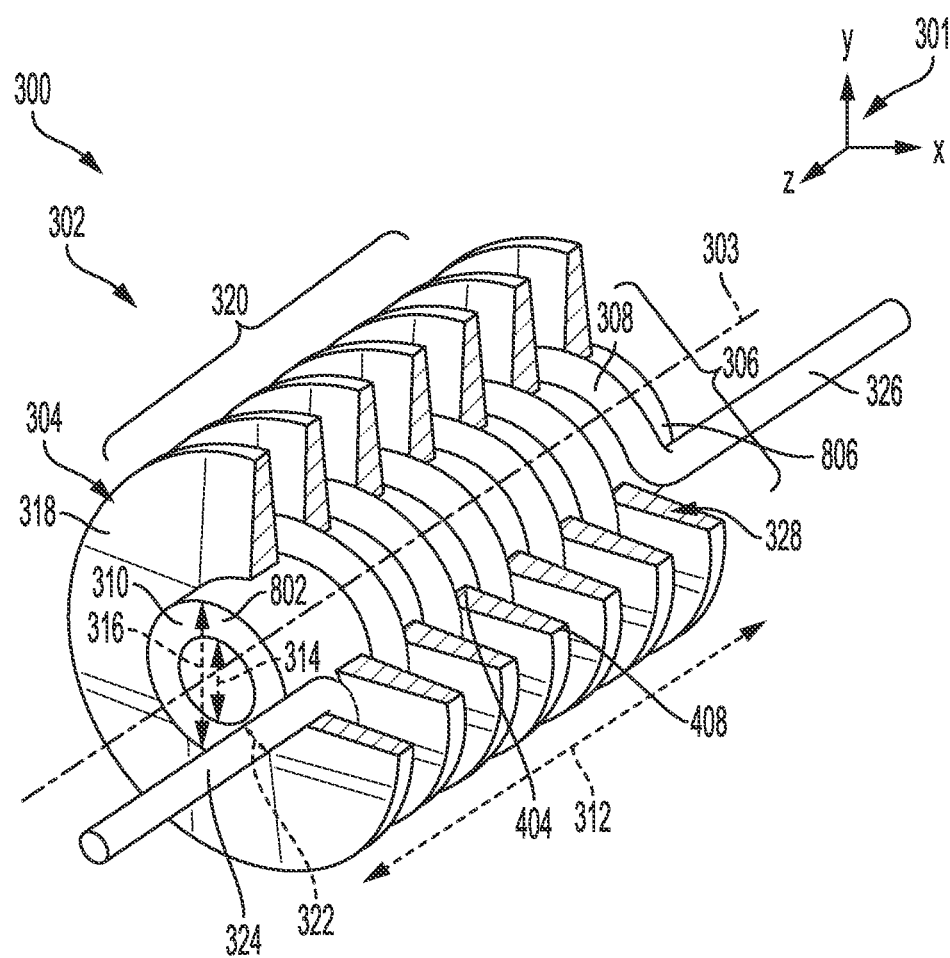
FIG. 3 is a perspective view of a current trap with a portion of a spiral core of the current trap removed according to an exemplary embodiment of the disclosure.
Figure 4:
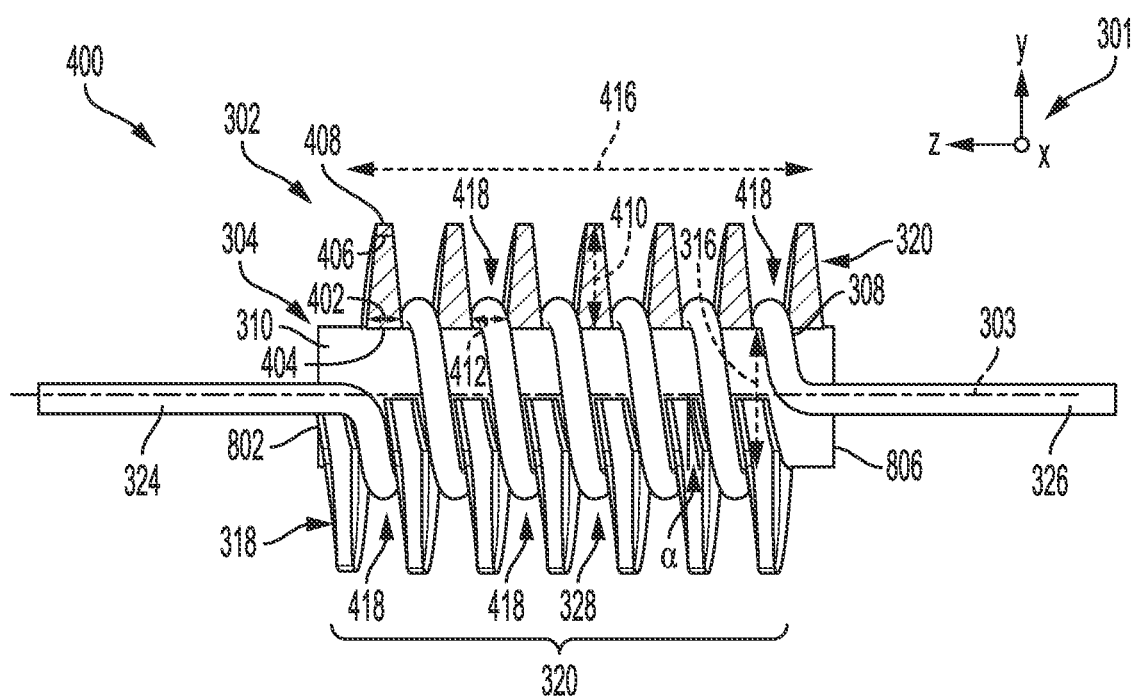
FIG. 4 is a side view of the current trap of FIG. 3.
Figure 5:
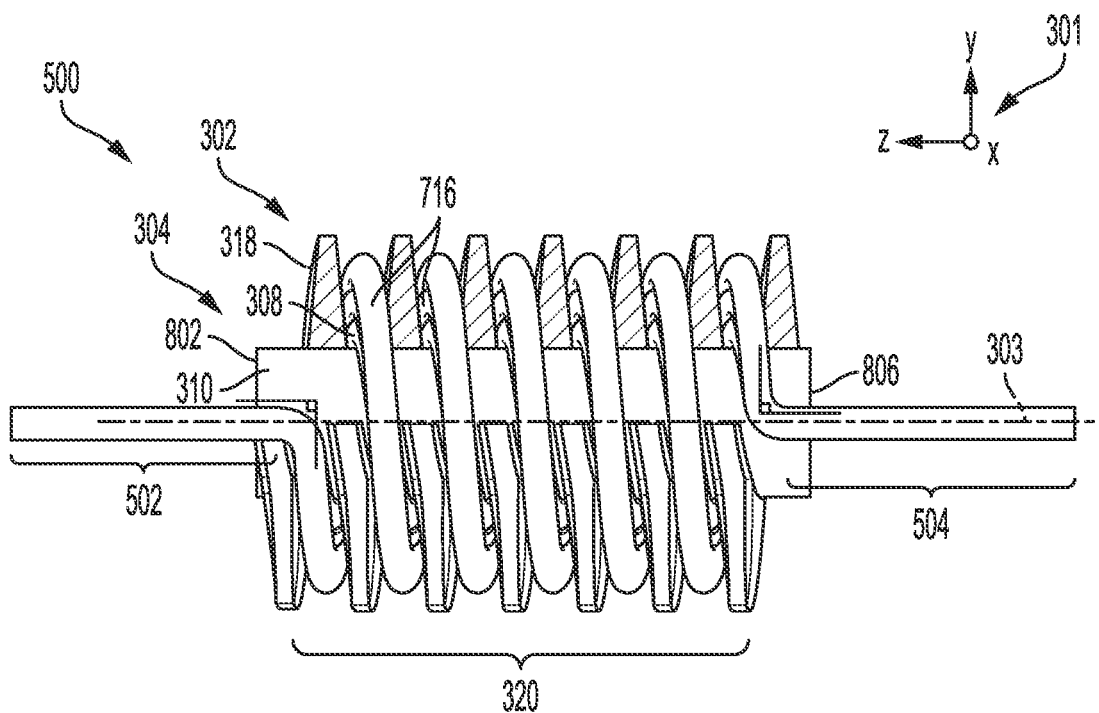
FIG. 5 is a side view of a floating current trap assembly with a portion of a spiral cores removed, showing the current trap coupled to cables according to an exemplary embodiment of the disclosure.
Figure 6:
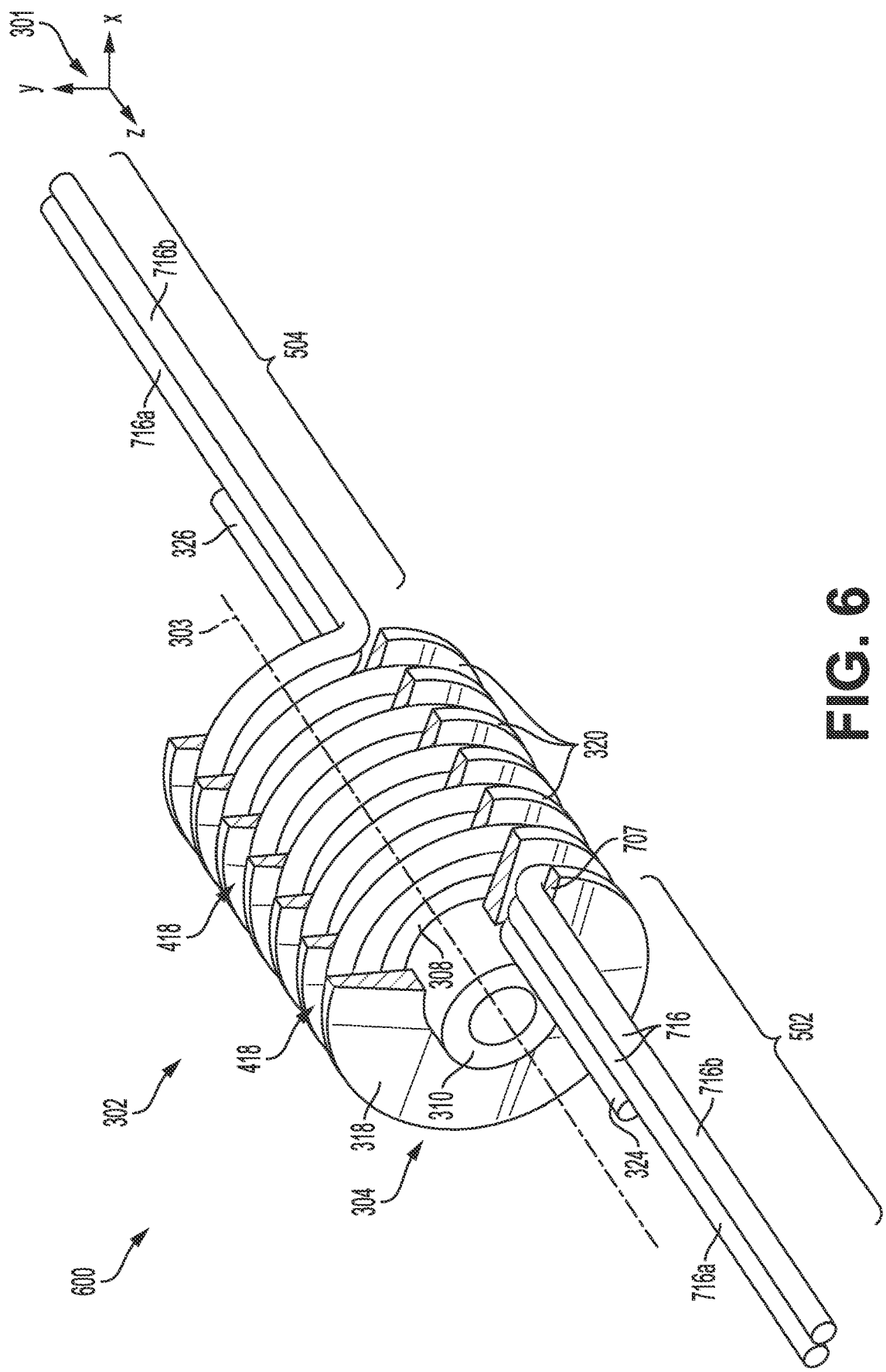
FIG. 6 is a perspective view of the floating current trap assembly of FIG. 5.
Figure 7:
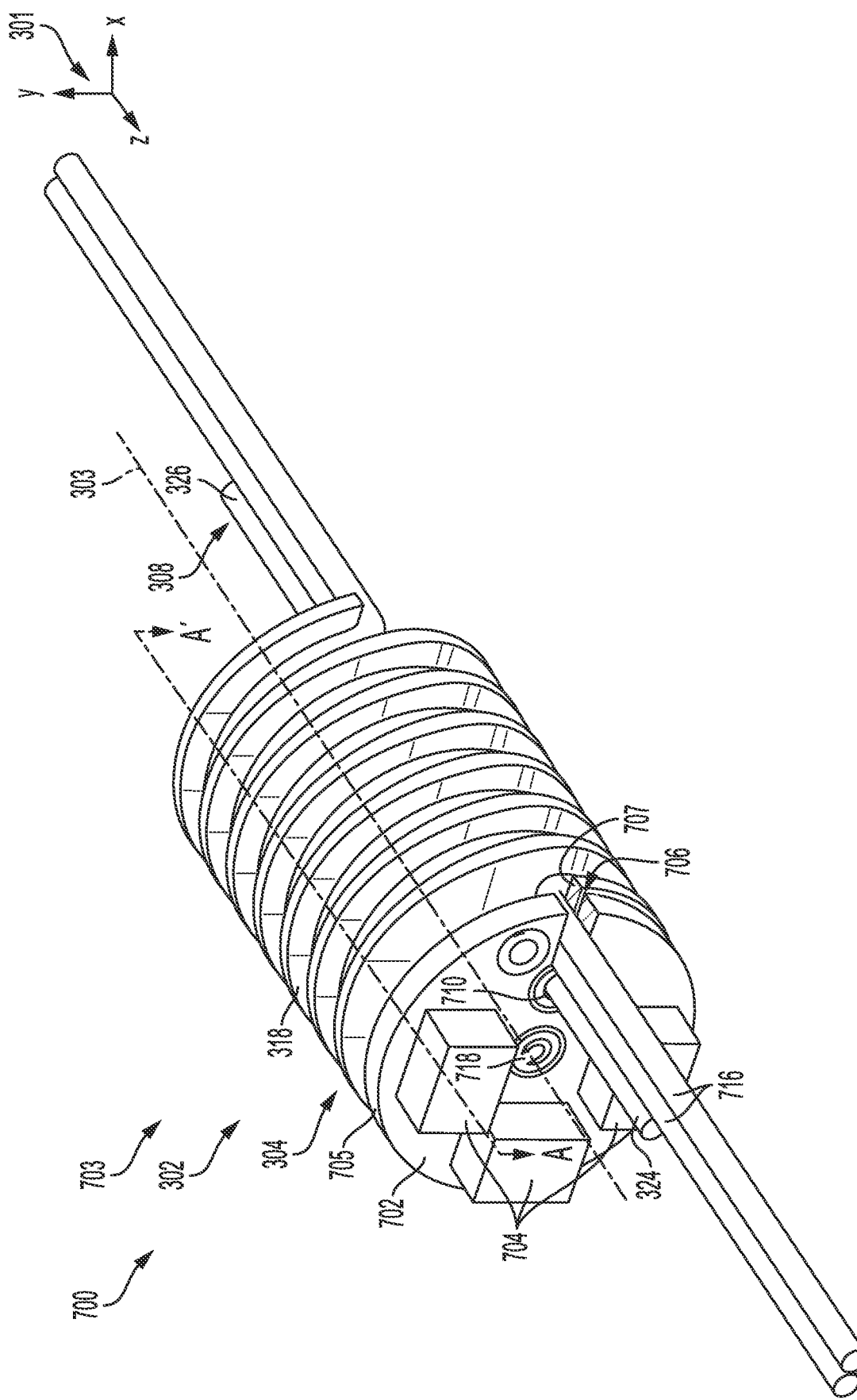
FIG. 7 is a perspective view of a floating current trap assembly according to an exemplary embodiment of the disclosure.
Figure 8:
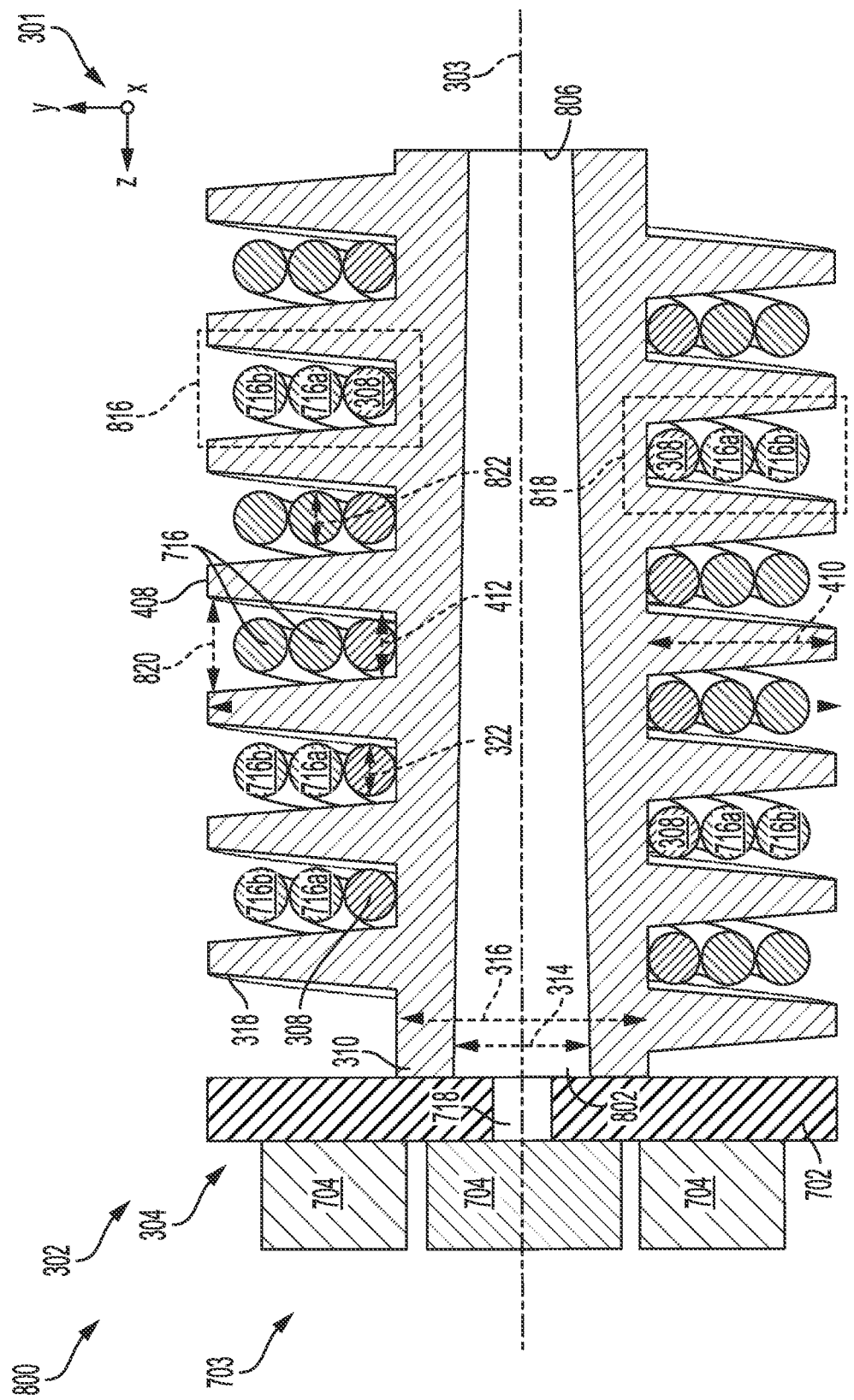
FIG. 8 is a cross-section of the floating current trap assembly of FIG. 7.
Figure 9:
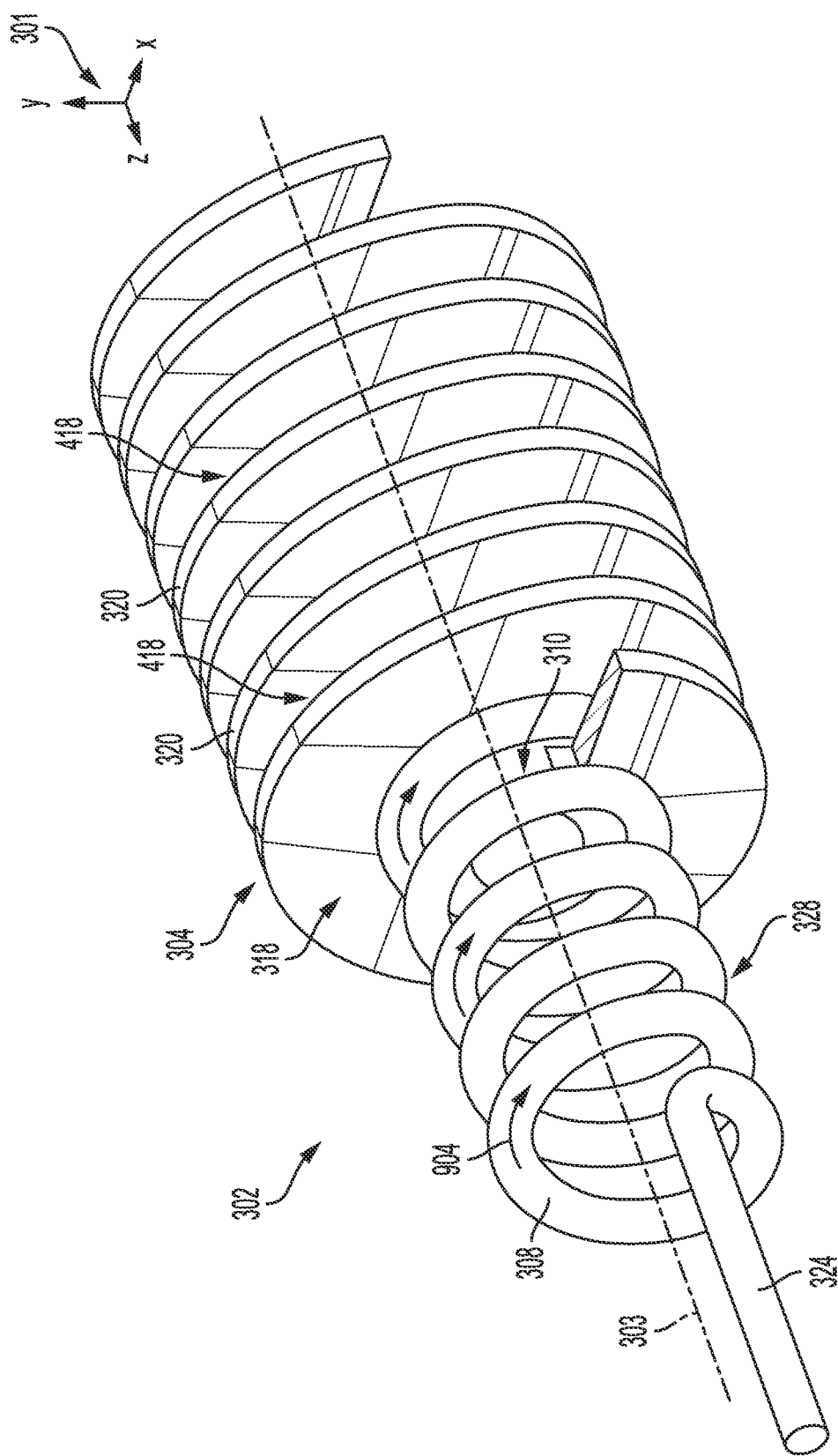
FIG. 9 is a perspective view of a coiled wire being assembled with a spiral core according to an exemplary embodiment of the disclosure.
Figure 10:
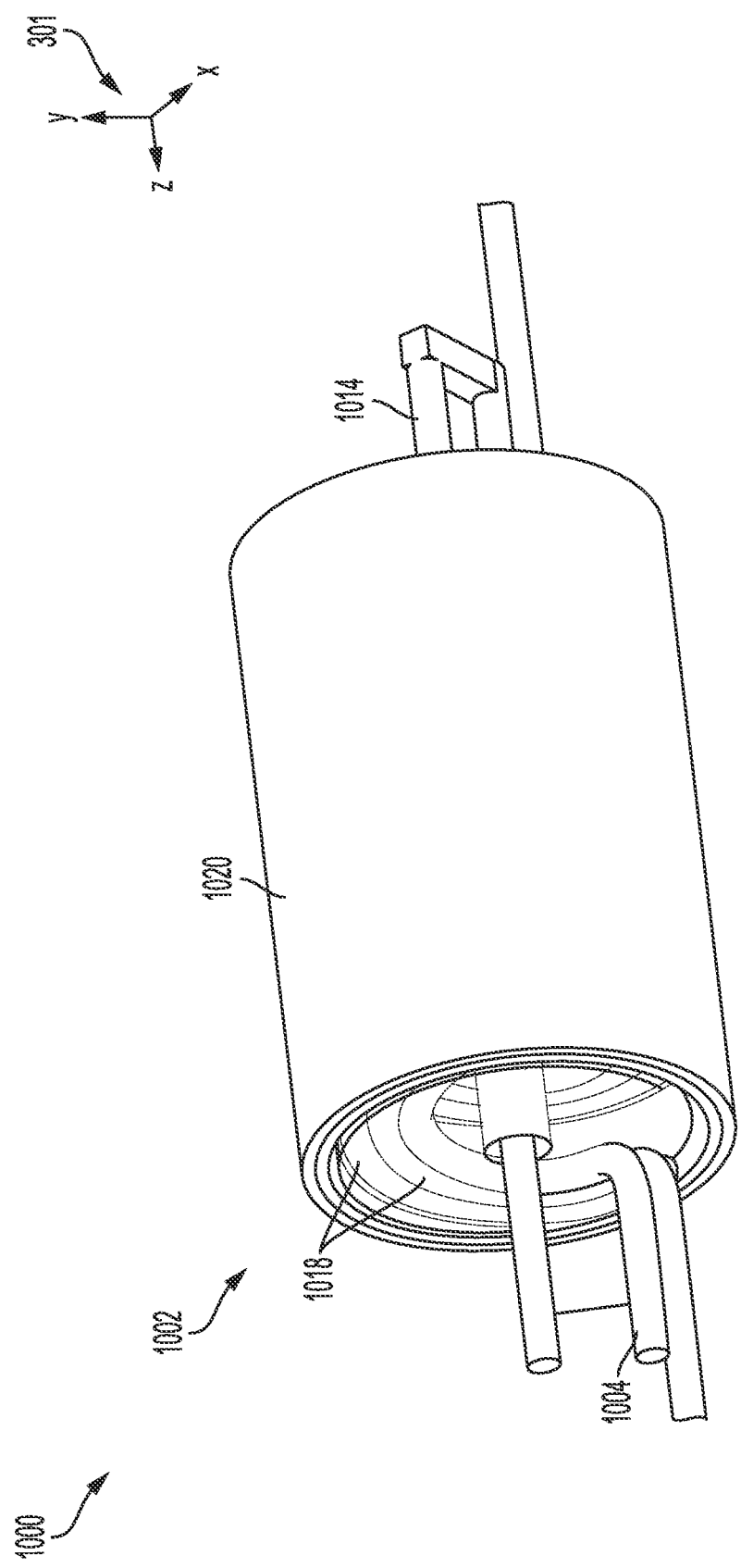
FIG. 10 is a perspective view of a shielded current trap according to an exemplary embodiment of the disclosure.
Figure 11:
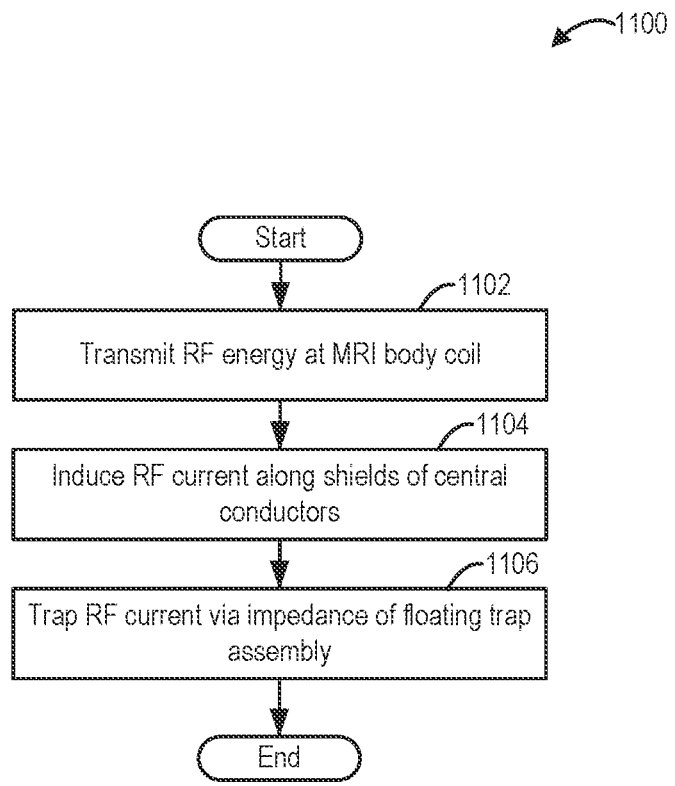
FIG. 11 is a high-level block diagram illustrating an example of a routine for a floating current trap assembly according to an exemplary embodiment of the disclosure.
Figure 12:
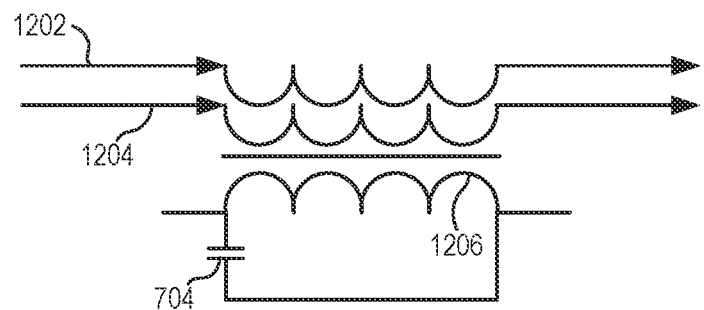
FIG. 12 is a schematic electrical circuit diagram of a floating current trap assembly according to an exemplary embodiment of the disclosure.
Figure 13:
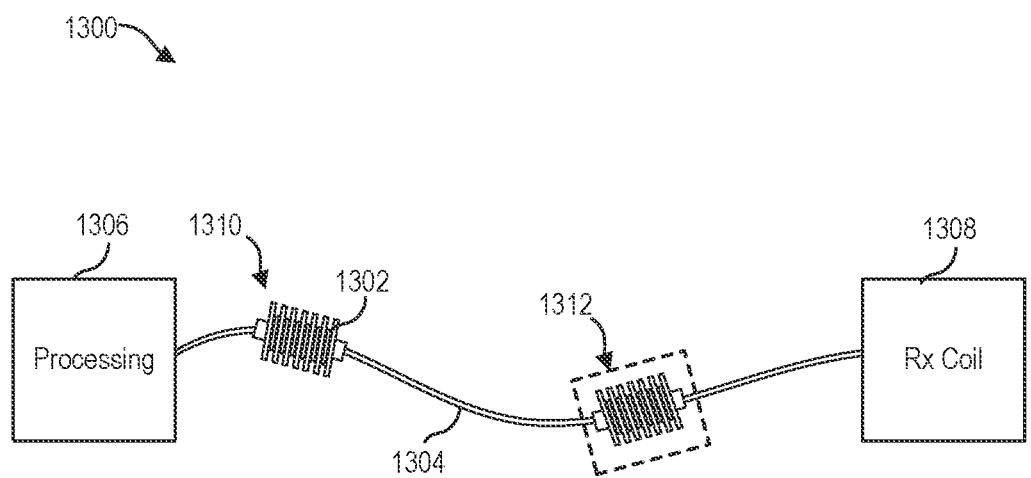
FIG. 13 illustrates an example of relocation of a floating current trap assembly along a coil-interfacing cable of an MRI system according to an exemplary embodiment of the disclosure.
Figure 14:
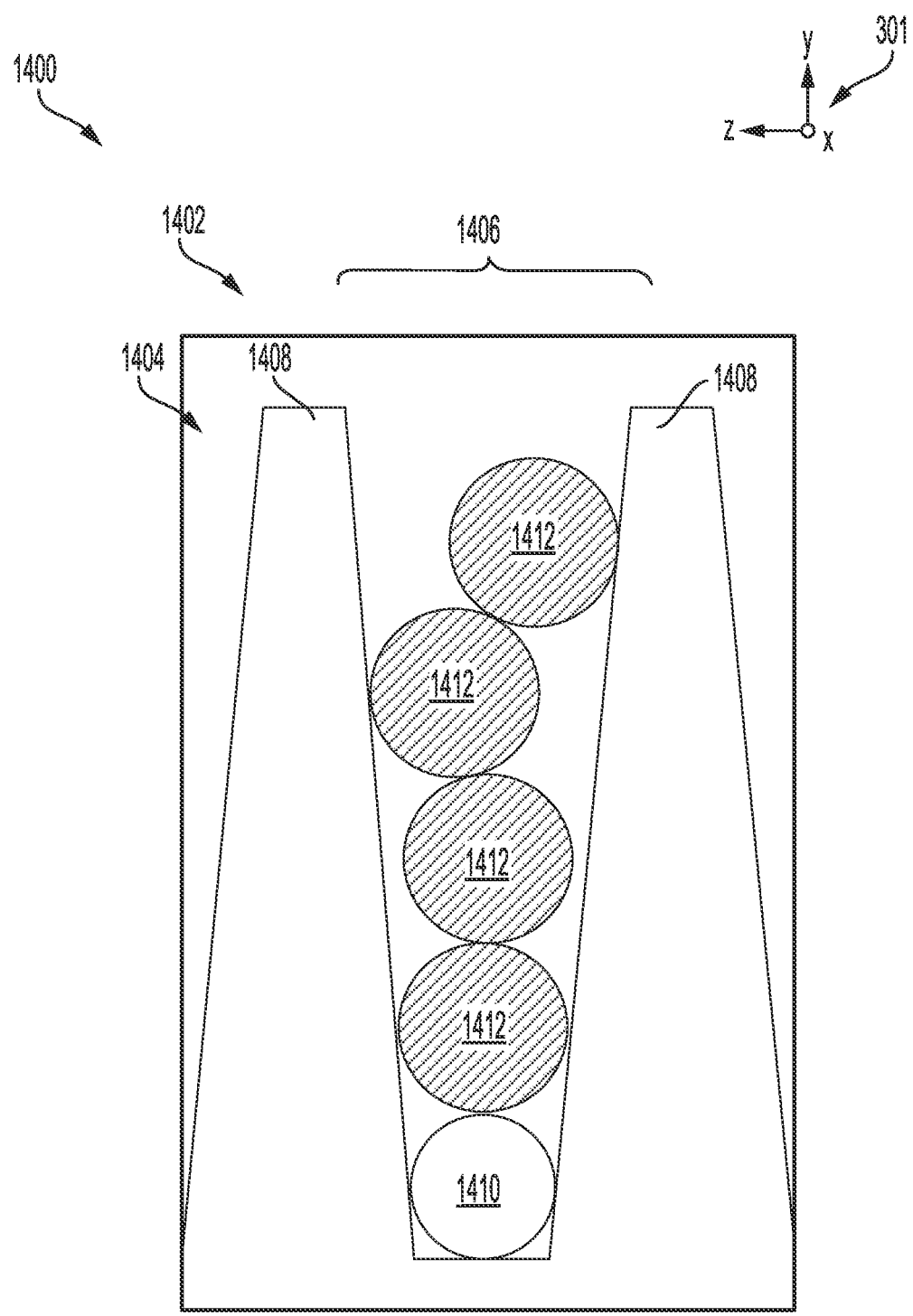
FIG. 14 is a detailed view of a current trap coupled to four cables.
Figure 15:
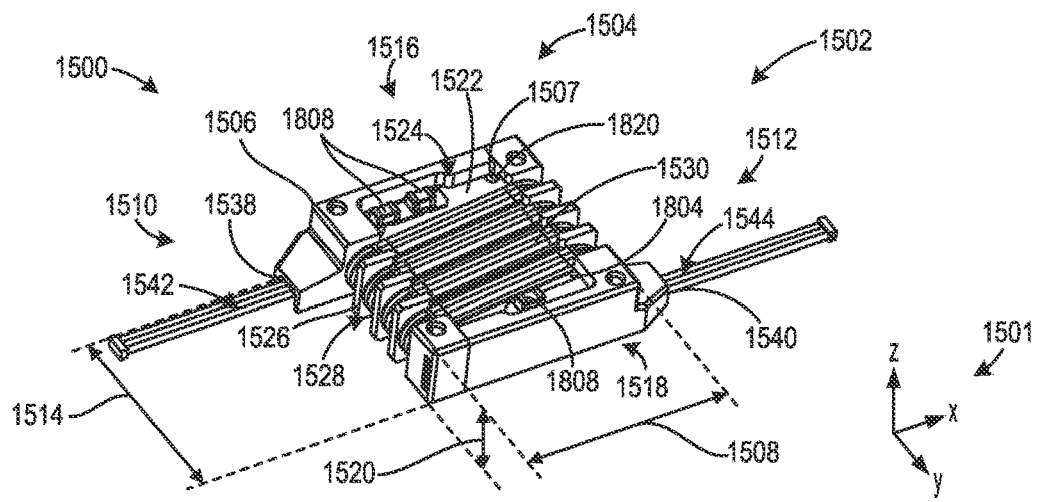
FIG. 15 is a perspective view of a floating current trap assembly according to another exemplary embodiment of the disclosure.
Figure 16:
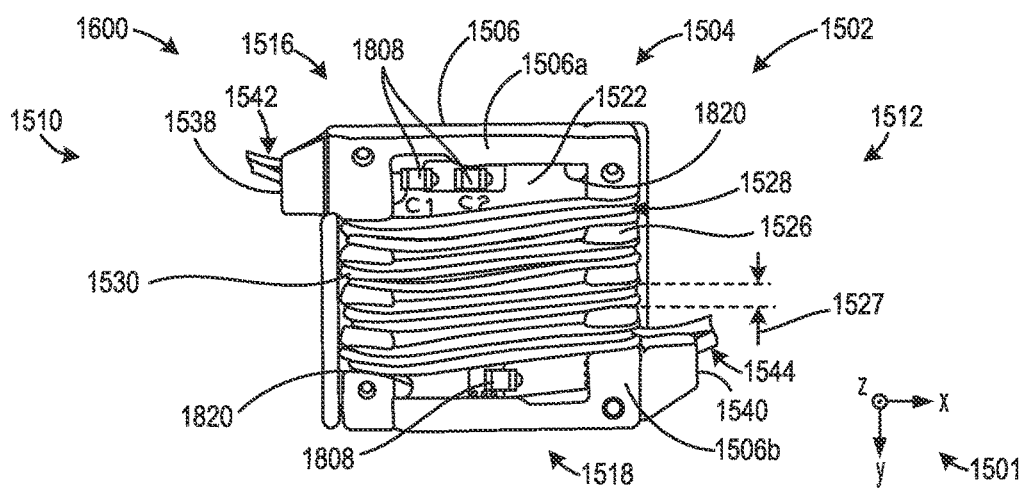
FIG. 16 is a top view of the current trap assembly of FIG. 15.
Figure 17:
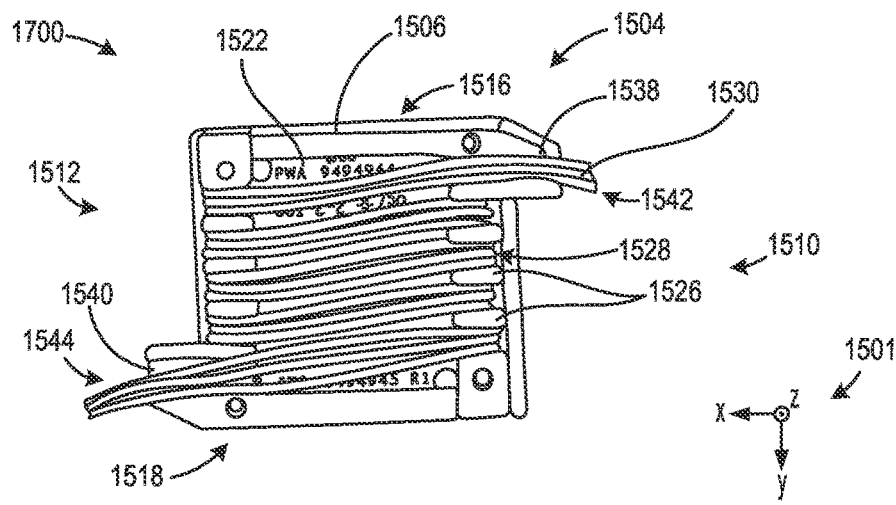
FIG. 17 is a bottom view of the current trap assembly of FIG. 15.

The following description relates to various embodiments for a current trap for MRI systems. In particular, systems are provided for a floating spiral configuration for a current trap for an MRI system, such as the MRI system illustrated in FIG. 1. Herein, a floating trap may be defined as a trap that may be removably coupled to cables of the MRI system by mechanical engagement and without additional processes to secure the trap to the cables, such as soldering. Furthermore, coupling the floating trap to the cables, unlike non-floating current traps, does not demand cutting of the cables, thus allowing a position of the floating trap to be readily reconfigured along the cables. As shown in FIG. 2, a current trap may be arranged along a communication cable configured to receive MR data. The current trap may be a floating trap as depicted in FIGS. 3 and 4. The current trap may be assembled by engaging a coiled wire with a spiral core, as shown in FIG. 9. The current trap may be configured to engage with cables of the MRI system by winding the cables around the spiral core, as illustrated in FIGS. 5 and 6. As illustrated in FIG. 14, the current trap may be coupled to up to four cables. A floating trap assembly is shown in FIG. 7 and a cross-section of the assembly is shown in FIG. 8. The current trap may be further covered with a shield, as illustrated in FIG. 10, when the current trap is to be positioned proximate to a patient. A routine for blocking transmission-induced currents along cable of an MRI system by implementing the floating trap is depicted in FIG. 11. A schematic of an electrical circuit of the floating trap is shown in FIG. 12, and a repositioning of the floating trap along a cable of an MRI system is illustrated in FIG. 13. Another example of a floating current trap is depicted in FIGS. 15-17, and a plurality of layers of a printed circuit board for use with the floating current trap of FIGS. 15-17 is illustrated in FIGS. 18-20. FIG. 21 depicts electrical connections between the layers of the PCB shown in FIGS. 18-20 designed to form resonant circuitry within the floating current trap of FIGS. 15-17. Another exemplary current trap which may include one or more covers and/or shields is illustrated in FIG. 22.

FIGS. 3-10, 14-20, and 21-22 show example configurations with relative positioning of the various components. If shown directly contacting each other, or directly coupled, then such elements may be referred to as directly contacting or directly coupled, respectively, at least in one example. Similarly, elements shown contiguous or adjacent to one another may be contiguous or adjacent to each other, respectively, at least in one example. As an example, components laying in face-sharing contact with each other may be referred to as in face-sharing contact. As another example, elements positioned apart from each other with only a space there-between and no other components may be referred to as such, in at least one example. As yet another example, elements shown above/below one another, at opposite sides to one another, or to the left/right of one another may be referred to as such, relative to one another. Further, as shown in the figures, a topmost element or point of element may be referred to as a "top" of the component and a bottommost element or point of the element may be referred to as a "bottom" of the component, in at least one example. As used herein, top/bottom, upper/lower, above/below, may be relative to a vertical axis of the figures and used to describe positioning of elements of the figures relative to one another. As such, elements shown above other elements are positioned vertically above the other elements, in one example. As yet another example, shapes of the elements depicted within the figures may be referred to as having those shapes (e.g., such as being circular, straight, planar, curved, rounded, chamfered, angled, or the like). Further, elements shown intersecting one another may be referred to as intersecting elements or intersecting one another, in at least one example. Further still, an element shown within another element or shown outside of another element may be referred as such, in one example.

Figure 1:
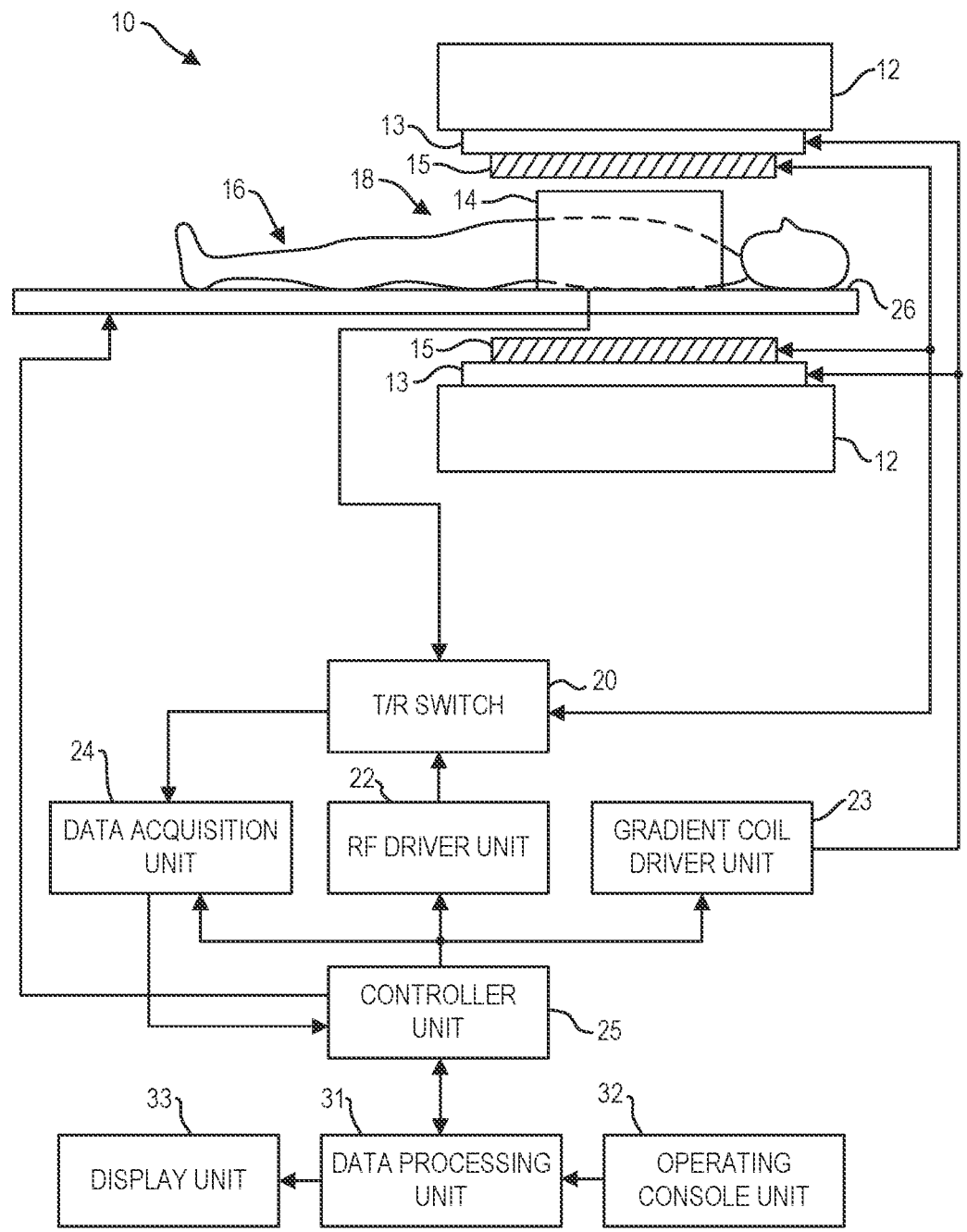
FIG. 1 is a block diagram of an MRI system according to an exemplary embodiment of the disclosure.

FIG. 1 illustrates a magnetic resonance imaging (MRI) apparatus 10 that includes a magnetostatic field magnet unit 12, a gradient coil unit 13, an RF coil unit 14, an RF body coil unit 15, a transmit/receive (T/R) switch 20, an RF driver unit 22, a gradient coil driver unit 23, a data acquisition unit 24, a controller unit 25, a patient bed 26, a data processing unit 31, an operating console unit 32, and a display unit 33. The MRI apparatus 10 transmits electromagnetic pulse signals to a subject 16 placed in an imaging space 18 with a magnetostatic field formed to perform a scan for obtaining magnetic resonance signals from the subject 16 to reconstruct an image based on the magnetic resonance signals thus obtained by the scan.

The magnetostatic field magnet unit 12 includes, for example, typically an annular superconducting magnet, which is mounted within a toroidal vacuum vessel. The magnet defines a cylindrical space surrounding the subject 16, and generates a constant primary magnetostatic field.

The MRI apparatus 10 also includes a gradient coil unit 13 that forms a gradient magnetic field in the imaging space 18 so as to provide the magnetic resonance signals received by the RF coil unit 14 with three-dimensional positional information. The gradient coil unit 13 includes three gradient coil systems, each of which generates a gradient magnetic field which inclines into one of three spatial axes perpendicular to each other, and generates a gradient field in each of frequency encoding direction, phase encoding direction, and slice selection direction in accordance with the imaging condition.

The RF coil unit 14 is disposed, for example, to enclose the region to be imaged of the subject 16. In the static magnetic field space or imaging space 18 where a static magnetic field is formed by the magnetostatic field magnet unit 12, the RF coil unit 14 may transmit, based on a control signal from the controller unit 25, an RF pulse to the subject 16. This excites a spin of protons in the subject 16. The RF coil unit 14 may also receive magnetic resonance signals generated when the proton spin thus excited in the subject 16 returns into alignment with the initial magnetization vector. The RF coil unit 14 may transmit RF excitation and receive MR signal using the same RF coil.

The RF body coil unit 15 is disposed, for example, to enclose the imaging space 18, and produces RF pulses within the imaging space 18 to excite the nuclei. In contrast to the RF coil unit 14, which may be easily disconnected from the MR apparatus 10 and replaced with another RF coil unit, the RF body coil unit 15 is fixedly attached and connected to the MR apparatus 10.

The T/R switch 20 can selectively connect the RF body coil unit 15 to the data acquisition unit 24 when operating in receive mode, and to the RF driver unit 22 when operating in transmit mode. Similarly, the T/R switch 20 can selectively connect the RF coil unit 14 to the data acquisition unit 24 when the RF coil unit 14 operates in receive mode, and to the RF driver unit 22 when operating in transmit mode. When the RF coil unit 14 and the RF body coil unit 15 are both used in a single scan, for example if the RF coil unit 14 is configured to receive MR signals and the RF body coil unit 15 is configured to transmit RF signals, then the T/R switch 20 may direct control signals from the RF driver unit 22 to the RF body coil unit 15 while directing received MR signals from the RF coil unit 14 to the data acquisition unit 24. The coils of the RF body coil unit 15 may be configured to operate in a transmit-only mode, a receive-only mode, or a transmit-receive mode. The coils of the local RF coil unit 14 may be configured to operate in a transmit-receive mode or a receive-only mode.

The RF driver unit 22 may include a gate modulator (not shown), an RF power amplifier (not shown), and an RF oscillator (not shown). The RF driver unit 22 modulates, based on a control signal from the controller unit 25 and using the gate modulator, the RF signal received from the RF oscillator into a signal of predetermined timing having a predetermined envelope. The RF signal modulated by the gate modulator is amplified by the RF power amplifier and then output to the RF coil unit 14.

The gradient coil driver unit 23 drives the gradient coil unit 13 based on a control signal from the controller unit 25 and thereby generates a gradient magnetic field in the imaging space 18. The gradient coil driver unit 23 may include three systems of driver circuits (not shown) corresponding to the three gradient coil systems included in the gradient coil unit 13.

The data acquisition unit 24 may include a preamplifier (not shown), a phase detector (not shown), and an analog/digital converter (not shown). The phase detector phase detects, using the output from the RF oscillator of the RF driver unit 22 as a reference signal, the magnetic resonance signals received from the RF coil unit 14 and amplified by the preamplifier, and outputs the phase-detected analog magnetic resonance signals to the analog/digital converter for conversion into digital signals. The digital signals thus obtained are output to the data processing unit 31.

The MRI apparatus 10 includes a table 26 for placing the subject 16 thereon. The subject 16 may be moved inside and outside the imaging space 18 by moving the table 26 based on control signals from the controller unit 25.

The controller unit 25 includes a computer and a recording medium on which a program to be executed by the computer is recorded. The program when executed by the computer causes various parts of the apparatus to carry out operations corresponding to an MRI scan.

The operating console unit 32 may include user input devices such as a keyboard and a mouse. The operating console unit 32 is used by an operator, for example, to input such data as an imaging protocol and to set a region where an imaging sequence is to be executed. The data about the imaging protocol and the imaging sequence execution region are output to the controller unit 25.

The data processing unit 31 includes a computer and a recording medium on which a program to be executed by the computer to perform data processing is recorded. The data processing unit 31 is connected to the controller unit 25 and performs data processing based on control signals received from the controller unit 25. The data processing unit 31 is also connected to the data acquisition unit 24 and generates spectrum data by applying various image processing operations to the magnetic resonance signals output from the data acquisition unit 24.

The display unit 33 includes a display device and displays an image and/or other information on the display screen of the display device based on control signals received from the controller unit 25. The display unit 33 displays, for example, scanning parameters. The display unit 33 also displays an MR image of the subject 16 generated by the data processing unit 31.

During a scan, coil-interfacing cables (not shown) may be used to transmit signals between the RF coils (e.g., RF coil unit 14) and other aspects of the processing system (e.g., data acquisition unit 24, controller unit 25, and so on), for example to control the RF coils and/or to receive information from the RF coils. In some embodiments, the coil-interfacing cables are integrated into the RF coil unit 14. The coil-interfacing cables may be disposed within the bore or imaging space 18 of the MRI apparatus 10 and subjected to electro-magnetic fields produced and used by the MRI apparatus 10. The cables may be subject to transmitter driven common mode currents which create field distortions and/or unpredictable heating of components. Baluns or common mode traps that provide high common mode impedances may be utilized to mitigate the effect of transmitter driven currents. Various embodiments of such common mode traps and common mode trap assemblies are described further herein.

FIG. 2 illustrates a block schematic diagram of a common mode trap assembly 200 or balun assembly 200. The balun assembly 200 may be configured, for example, for use in the bore of an MRI system, such as the MRI apparatus 10 described herein above. For example, in the illustrated embodiment, the balun assembly 200 is configured as a transmission cable 201 configured for transmission of signals between a processing unit (or controller) 250 and a receive coil 260 of an MRI system. In some embodiments, the transmission cable 201 is integrated into the receive coil 260 and becomes part of it. The receive coil 260 further includes one or more coil elements coupled to the transmission cable, as known in the art.

In the illustrated embodiment, the transmission cable 201 (or balun assembly 200) includes a central conductor 210 and at least one balun 212. The central conductor 210 in the illustrated embodiment has a length 204, and is configured to transmit a signal between the MRI receive coil 260 and at least one processor of an MRI system (e.g., processing unit 250). The central conductor 210 may include one or more of a ribbon conductor, a wire, or a coaxial cable bundle, for example.

The depicted balun 212, as seen in FIG. 2, extends along at least a portion of the length 204 of the central conductor 210. In the illustrated embodiment, balun 212 does not extend along the entire length 204. However, in other embodiments, the balun 212 may extend along the entire length 204, or substantially along the entire length 204.

The balun 212 is configured to provide an impedance to the receive transmitter driven currents of an MRI system. The balun 212 in various embodiments provides high common mode impedances. For example, the balun 212 may include a resonant circuit and/or one or more resonant components to provide a high impedance at or near a desired frequency or within a target frequency range. It may be noted that the balun 212 may also be referred to as a choke by those in the art.

The balun 212 may be tuned to have a resonant frequency near an operating frequency of the MRI system. As used herein, a balun may be understood as having a resonant frequency near an operating frequency when the resonant frequency defines or corresponds to a band that includes the operating frequency, or when the resonant frequency is close enough to the operating frequency to provide on-frequency blocking, or to provide a blocking impedance at the operating frequency.

In conventional designs, the balun has a central opening through which the central conductor passes and the balun is usually soldered to the central conductor. Such soldering process may be complex and may expose the central conductor to high temperatures. The central conductor, adapted for RF applications, may be sensitive to heat and soldering the central conductor may result in degradation of the central conductor. The present disclosure describes an implementation of a balun that may be installed without soldering or any special complex process. Additionally, the balun may be removed and reinstalled without causing any wire degradation.

An exemplary embodiment of a balun 302 is shown in FIGS. 3-9. The balun 302 may be a current trap 302 shown in FIGS. 3 and 4 in a first view 300 and a second view 400, respectively, without being coupled to any cables yet. Furthermore, the current trap 302 may be an unshielded current trap. A set of reference axes 301 are provided, indicating a y-axis, an x-axis, and a z-axis. The current trap has a central axis 303 which is parallel with the z-axis.

The current trap 302 may be a generally cylindrical structure formed of two portions: a spiral core 304, and a coiled wire 308. The spiral core 304 may be formed of a rigid, durable, nonconductive (e.g., insulating) material, such as plastic, and provides a frame for the current trap 302. A central tube 310 of the spiral core 304 may extend along an entire length 312 of the spiral core 304 along the central axis 303. The length 312 of the spiral core 304 may be different depending on an application of the current trap 302. For example, a diameter and length of a cable to which the current trap 302 is coupled may affect the length 312 of the spiral core. As an example, the length 312 of the spiral core 304 may be 3.5 cm. An inner diameter 314 of the central tube 310 may be, for example, 0.2-0.5 cm while an outer diameter 316 of the central tube 310 may be 0.4-0.7 cm. The inner diameter 314 and the outer diameter 316 may be uniform along the length 312 of the spiral core 304. Alternatively, as shown in a cross-section 800 in FIG. 8, the inner diameter 314 may taper between a first end 802 and a second end 806 of the central tube 310 for plastic piece tooling. However, in other embodiments, the inner diameter 314 may remain uniform between the first end 802 and the second end 806.

A spiral rib 318 may be disposed at an outer surface of the central tube 310, protruding radially outwards from the central axis 303. The spiral rib 318 may provide insulation between each turn of the coiled wire 308, where each turn is a full 360 degree rotation around the central axis 303. In other words, each turn of the coiled wire 308 is spaced away from adjacent turns by the spiral rib 318, thereby electrically insulating each turn. The spiral core 304 may be fabricated, by injection molding, for example, so that the spiral rib 318 and the central tube 310 are made as one piece. The spiral rib 318 may have a trapezoidal cross-section, e.g., when the cross-section is taken along the y-z plane as shown in FIG. 4. Therein, a width 402 of the spiral rib 318, defined along the z-axis, at a base 404 of the spiral rib 318 is greater than a width 406 of the spiral rib 318 at an outer edge or tip 408 of the spiral rib 318.

A height 410 of the spiral rib 318 may be equal to or greater than a sum of a diameter 322 of the coiled wire 308 plus a diameter of each cable coupled to the current trap 302. For example, as shown in FIG. 8, the height 410 is equal to or greater than the sum of the diameter 322 of the coiled wire, a diameter of a first cable 716a and a diameter of a second cable 716b. The spiral rib 318 protrudes radially outwards, away from the central tube 310, and coils around the central tube 310 to form a plurality of layers 320. The plurality of layers 320 are continuous with one another but are seen individually in the cross-sectional view in FIG. 4.

The height 410 of the spiral rib 318 remains substantially uniform along the length 312 of the spiral core 304. Thus, each of the plurality of layers 320 are similar in shape and size. The uniform height of the spiral rib 318 results in a cylindrical outer geometry of the spiral core 304. As shown in FIG. 4, the plurality of layers 320 are spaced uniformly apart along the length 312 of the spiral core 304. A distance between each of the plurality of layers 320 at the base 404 of each layer may be a pitch 412 of the spiral rib 318. The pitch 412 may be similar to, narrower, or wider than the width 402 of the spiral rib 318 at the base 404 of the spiral rib 318.

The pitch 412 of the spiral rib 318 may be configured to accommodate winding of the coiled wire 308 so that the coiled wire 308 is inserted between each of the plurality of layers 320 at the base 404 of each of the plurality of layers 320. As such, the pitch 412 of the spiral rib 318 may be similar to or larger than the diameter 322 (shown in FIG. 3) of the coiled wire 308. The pitch 412 of the spiral rib 318 may be different according to the thickness of the coiled wire 308. For example, if a thicker coiled wire 308 is to be inserted into the spiral core 304, the pitch 412 of the spiral rib 318 may be made larger. Conversely, if a thinner coiled wire 308 is to be inserted, the pitch 412 may be made smaller. The length 312 of the spiral core 304 may also be varied if a specific pitch and a specific number of the plurality of layers 320 is desired. Furthermore, a helix angle α, as shown in FIG. 4, indicates an angle of a spiraling of the spiral rib 318 relative to the y-axis.

The coiled wire 308 is wound around the central tube 310 along the spiral rib 318. In some embodiments, the coiled wire 308 includes a first straight section 324 and a second straight section 326, and a central portion 328, positioned between the first straight section 324 and the second straight section 326 and coiled around the central tube 310 of the spiral core 304. In some embodiments, the coiled wire 308 includes only the central portion 328, which forms an inductor and enables the current trap 302 to interact with coil-interfacing cables through electromagnetic induction. The coil-interfacing cables may be shielded and a current, e.g., a shield current, may be induced at a grounding shield of the coil-interfacing cables when current flows through the coil-interfacing cables. The central portion 328 of the coiled wire 308 generates an electromagnetic field when the shield current flows through the coil-interfacing cables, which impedes the shield current via a resonant circuit of the current trap 302, as described further below. The coiled wire 308 may be a conductor made of any appropriate conductive material, such as copper, aluminum, etc., but not ferromagnetic materials.

A length 416 of the central portion 328, as shown in FIG. 4, may be similar to or shorter than the length 312 of the spiral core 304. The central portion 328 may have a number of turns equal to or fewer than a number of spaces 418 in between the plurality of layers 320 of the spiral core 304. In FIG. 4, the central portion 328 has six turns, corresponding to six spaces 418 between the plurality of layers 320. However, other numbers of turns of the central portion 328 of the coiled wire 308 and of spaces 418 between the plurality of layers 320 have been contemplated, such as 4, 7, 8, etc.

As described above, the central portion 328 of the coiled wire 308 is in contact with and wraps around the central tube 310 of the spiral core 304. The central portion 328 has a helical configuration and each turn of the central portion 328 coils around the central tube 310 of the spiral core 304 along a uniform angle relative to the y-axis, which may be equal or close to the helix angle α.

FIG. 9 shows the coiled wire 308 being coupled to the spiral core 304. The central portion 328 may be fed into the spaces 418 between the plurality of layers 320 by turning the coiled wire 308 in a rotational direction indicated by arrows 904. The coiled wire 308 may be rotated until all turns of the central portion 328 are engaged in the spaces 418. The engagement of the coiled wire 308 with spiral core 304 forces the turns of the coiled wire 308 to be spaced apart by the pitch 412 of the spiral core 304.

The current trap 302 may further include one or more tuning capacitors that form a resonant circuit with the coiled wire 308 which functions as an inductor in the circuitry. A printed circuit board (PCB) 702 may carry the tuning capacitors, as shown in a perspective view 700 and in the cross-section view 800 of FIG. 8, taken along line A-A' of FIG. 7. The PCB 702 may carry a set of tuning capacitors 704, each tuning capacitor spaced apart from the other tuning capacitors 704 and arranged on an outward facing surface of the PCB 702, e.g., a surface of the PCB 702 facing away from the spiral core 304 of the current trap 302. The current trap 302 may be tuned by coupling a probe to the PCB 702 to adjust the impedance to block a target frequency, such as 127.7 MHz, before the current trap assembly 703 is coupled to the coil-interfacing cable. In other words, the current trap assembly 703 may be pre-tuned during manufacturing and provided to a user as a tuned, ready-to-use device.

The PCB 702 may be coupled to the first end 802 (as shown in FIG. 8) of the central tube 310 of the spiral core 304 by an adhesive. It will be appreciated that the PCB 702 may be similarly coupled to the second end 806 of the central tube 310 of the spiral core 304 without affecting a tuning capacity of the set of tuning capacitors 704. The PCB 702 may include a slot 706, as shown in FIG. 7 extending from an outer edge 705 of the PCB 702 towards the central axis 303 and terminating at a rounded end 710 disposed between the outer edge 705 of the PCB 702 and the central axis 303. The rounded end 710 of the slot may align with the first section 324 of the coiled wire 308 along the z-axis, allowing the first section 324 of the coiled wire 308 to extend through the rounded end 710. The rounded end 710 may be lined with a conductive material, such as a copper gasket, and functions as a first electrical connection end for the set of capacitors 704. In some embodiments, the rounded end 710 is made in contact with the first section 324 of the coiled wire 308 via soldering, to electrically couple the set of tuning capacitors 704 of the PCB 702 to the coiled wire 308 at one end.

The PCB 702 may also have a central aperture 718 aligned with the central axis 303 and extending entirely through a thickness of the PCB 702, as shown in FIG. 8, where the thickness is defined along the z-axis. A bus wire functions as a second electrical connection end for the set of capacitors 704 and passes through the central aperture 718 of the PCB 702. The bus wire continues to pass through the central tube 310 from the first end 802 all the way to the second end 806 and is made in contact with the second section 326 of the coiled wire 308 via soldering, to electrically couple the set of tuning capacitors 704 of the PCB 702 to the coiled wire 308 at another end.

The PCB 702 may be configured as a circular disc as shown in FIGS. 7 and 8. A variety of conductive tracks, pads and other features may be etched into laminated sheets of copper and electrical components, such as the set of tuning capacitors 704, may be soldered on to the PCB 702. The set of tuning capacitors 704 may be spaced away from one another. In some embodiments, the inductor formed by the coiled wire 308 is connected to the set of capacitors 704 by connecting two ends of the coiled wire 308 to two ends of the capacitor set 704 respectively, as described above.

One or more cables may be wound around the spiral core 304 and stacked on top of the coiled wire 308 to form a floating trap assembly. FIGS. 7 and 8 show two cables 716 wound around the spiral core 304 and stacked on top of the coiled wire 308. An equivalent electrical circuit diagram of this floating trap assembly is shown in FIG. 12. The inductor 1206 (e.g., central portion 328 of coiled wire 308) and the tuning capacitor(s) 704 form a resonant circuit. Cables 1202 and 1204 (e.g., coil-interfacing cables in an MRI system) are coupled to the inductor 1206 via electromagnetic interaction. The resonant circuit has a high impedance to shield currents generated in cables 1202 and 1204 and can reduce the shield currents through the electromagnetic coupling with cables 1202 and 1204.

The cables 716 may be coil-interfacing cables, curving around a first end 707 of the spiral rib 318 and extending through the slot 706, as shown in FIGS. 6-8. Each of the cables 716 may include a shield. The shield may be a common conductive layer, formed of a material such as braided strands of metal, a spirally wound metallic tape, a conducting polymer, etc., that circumferentially surrounds each of the cables 716. As such, the shield encloses one or more insulated conductors, e.g., wires, of each of the cables 716. Implementing each of the cables 716 with the shield may reduce electrical noise which may otherwise degrade electrical signals transmitted by the cables 716. The shield may also decrease electromagnetic radiation which may cause electromagnetic interference with other electrical devices.

The conductive nature of the shield may result in an increased likelihood of generation of shield currents on the cables 716, which may cause localized heating of the cables 716, distortion of MRI images, and adversely affect coil tuning. Thus equipping the MRI system with at least one floating trap assembly 703 may circumvent the issues described above.

The coupling of the PCB 702 to the current trap 302 allows the floating trap assembly 703 to be tuned away from an MRI system and independent of the MRI system. Use of the floating trap assembly 703 may therefore be expedited by precluding a time-consuming tuning procedure. The tuning procedure may be performed during manufacturing of the floating trap assembly 703 where the set of tuning capacitors 704 may be adjusted to provide an impedance of the floating trap assembly 703 that blocks a resonant frequency of a shield current carried by the cables 716. Alternatively, the floating trap assembly 703 may be configured to block a range of frequencies to enable the floating trap assembly 703 to be used across a variety of systems with varying resonance frequencies to be impeded.

The cable(s) 716 may be wound around the spiral core 304 of the current trap 302 through the spaces 418 between the plurality of layers 320 of the spiral core 304, the spaces 418 shown in FIG. 4. The cable(s) 716 may be arranged so that the cables 716 are stacked along the y-axis within each of the spaces 418. The stacking of the cables 716 is shown in greater detail in FIGS. 5, 6 and 8. A side view 500 and a perspective view 600 of the current trap 302 coupled to the cables 716 is depicted in FIGS. 5 and 6, respectively. Similar to FIGS. 3-4, a section (e.g., indicated by bracket 306 in FIG. 3) of the spiral rib 318 of the spiral core 304 is removed for clarity. The cables 716 may be similar in diameter to the diameter 322 of the coiled wire 308 or may have diameters different from the coiled wire 308 or from one another in other examples.

A configuration of the cables 716, when coupled to the spiral core 304, may be similar to the configuration of the coiled wire 308. A first region 502 and a second region 504 of the cables 716, which are not coupled to the spiral core 304, may extend away from the spiral core 304 along the z-axis. The cables 716 may follow a similar geometry to the coiled wire 308 wrapping around the central portion 328 of the coiled wire 308 through the spaces 418 between the plurality of layers 320 along the helix angle α, as shown in FIG. 4 and extending away from the spiral core 304 at the first and second regions 502, 504, in opposite directions.

The stacking of the cables 716 and the coiled wire 308 along the spiral core 304 is further depicted in the cross-section 800 of FIG. 8. The cables 716 include the first cable 716a and the second cable 716b, as shown in a first dashed region 816. The first cable 716a is positioned directly adjacent to the coiled wire 308, in between the coiled wire 308 and the second cable 716b, as shown in the first and second regions 502, 504 of the cables 716 in FIG. 6. In other words, no other cables or objects are disposed between the first cable 716a and the coiled wire 308 along an entire length of the coiled wire 308.

As the cables 716 wind through the spiral core 304, the relative positioning of the first cable 716a, as shown in FIG. 8, is maintained in contact with the coiled wire 308 along the length 312 of the spiral core 304. In the first dashed region 816 of FIG. 8, the coiled wire 308 and the cables 716 are stacked along the y-axis, e.g., along a radial direction perpendicular to the central axis 303, with the first cable 716a on top of the coiled wire 308 and the second cable 716b on top of the first cable 716a. While the stacking of the coiled wire 308 and the cables 716 may be angled with respect to the y-axis, e.g., following the helix angle α as shown in FIG. 4, the coiled wire 308 and the cables 716 do not align parallel with the central axis 303 at any point along the spiral core 304.

A second dashed region 818 shows an arrangement of the coiled wire 308 and the cables 716 in an opposite side of the spiral core 304 from the first dashed region 816. The first cable 716a is positioned directly below the coiled wire 308 along the y-axis and the second cable 716b is positioned directly below the first cable 716a. Thus the relative positioning of the first cable 716a and second cable 716b is maintained along the spiral core 304 and around the spiral core 304.

Dimensions of the spaces 418 between the plurality of layers 320 of the spiral core 304 may be configured to accommodate cable diameters that differ from the diameter 322 of the coiled wire 308. The pitch 412 of the spiral rib 318 may be similar to the diameter 322 of the coiled wire 308. A width of the spaces 418 may increase along the y-axis towards the tip 408 of the spiral rib 318 (which are also tops 408 of the plurality of layers 320) so that a width 820 of the spaces 418 at the tops 408 of the spaces 418 is wider than the pitch 412 of the spiral core 304. The increase in width of the spaces 418 in a radial direction away from the central axis 303 enables a diameter 822 of each of the cables 716, which may be larger than the diameter 322 of the coiled wire 308, to fit within the spaces 418. However, the width 820 of the spaces 418 is maintained less than two times the diameter 822 of the cables 716 so that the cables may not shift.

The height 410 of the spiral rib 318 may be equal to or greater than a sum of the diameter 322 of the coiled rib 308 and the diameters 822 of the cables 716. Furthermore, the height 410 may be varied to accommodate more cables 716 than shown in FIGS. 5-7. The current trap 302 may be configured to couple to up to four cables 716, the cables 716 stacked similarly to the first and second cables 716a, 716b, as shown in FIG. 8, along the radial direction perpendicular to the central axis 303. An example of a current trap coupled to four cables is depicted in FIG. 14.

FIG. 14 shows a detailed view 1400 of a section of a current trap 1402 having a spiral core 1404 similarly configured to the spiral core 304 shown in FIGS. 3-9. A space 1406 between adjacent threads 1408 of the spiral core 1404 receives a coiled wire 1410 and four cables 1412. The cables 1412 are stacked on top, relative to the y-axis, of the coiled wire 1410 and on top of one another.

The floating trap assembly 703 may have several advantages over a conventional balun (e.g., non-floating). The coil-interfacing cables of the MRI system may be wrapped around the spiral core of the floating trap assembly without cutting the cables. Thus soldering of the floating trap assembly to the cables is not demanded, mitigating exposure of the cables to high temperature. As the floating trap assembly is a portable unit that is not anchored to any other structures, the floating trap assembly may be positioned anywhere along the cables without cutting the cables and may therefore be placed in convenient locations along the cables that allow the floating trap assembly to be readily accessed.

An example of how a floating trap assembly may be reconfigured along at least one coil-interfacing cable is depicted in a schematic diagram 1300 in FIG. 13. The current trap 1302 may be coupled to a cable 1304 extending between a processing unit 1306 and a receive coil 1308 of an MRI system. The current trap 1302 may be arranged at a first location 1310, closer to the processing unit 1306 than the receive coil 1308, and connected to the cable 1304 by winding the cable 1304 around a spiral core of the floating trap assembly 1302 on top of a coiled wire of the current trap 1302.

The floating trap assembly may be re-located to a second location 1312 along the cable 1304 by unwinding the cable 1304 from the spiral core of the current trap 1302 and moving the current trap 1302 along the cable, closer to the receive coil 1308. The current trap 1302 may be coupled to the cable 1304 by winding the cable 1304 around the spiral core of the current trap 1302. Furthermore, the floating trap assembly may be readily re-positioned to any point along the cable 1304 between the processing unit 1306 and the receive coil 1308.

Referring to FIG. 10, a shielded current trap 1002 is depicted in a perspective view 1000. Similar to the unshielded current trap shown in FIGS. 3-4, the shielded current trap 1002 may have a coiled wire 1004 coupled to a bus wire 1014 which functions as an electrical connection end for tuning capacitor(s). Additionally, the shielded current trap 1002 may be configured as a floating current trap. It will be appreciated that while the bus wire 1014 of FIG. 10 is not depicted in FIGS. 3-9 for brevity, the bus wire 1014 may be similarly coupled to the current trap 302 of FIGS. 3-9.

In addition to components of the unshielded current trap, the shielded current trap 1002 further comprises a shield 1020 enclosing the cables 1018. The shield 1020 is a hollow cylinder that encloses the spiral core, the coiled wire, and the cable. The shield 1020 may be formed of an electromagnetically insulating material such as plastic coated with an outer layer of copper tape. Furthermore, the shield 1020 may be provided as a sheet of the electromagnetically insulating material with a mechanism for coupling parallel edges of the sheet to one another. In this way, the cables 1018 may be first coiled around the spiral core and then the shield 1020 may be wrapped around the spiral core and maintained in the cylindrical geometry around the spiral core by fastening the parallel edges of the shield 1020 to one another. Implementing the shielded current trap 1002 with the shield 1020 may reduce the exposure of a patient to electromagnetic radiation.

Another exemplary embodiment of a balun 1502 is shown in FIGS. 15-17. The balun 1502 may be a current trap 1502 shown in a first view 1500 in FIG. 15. The current trap is shown in a second (e.g., top) view 1600 and a third (e.g., bottom) view 1700 in FIGS. 16 and 17, respectively. Further, the current trap 1502 may be an unshielded current trap having a flat core about which one or more cables 1530 (e.g., transmission cables, such as ribbon conductors, wires, or coaxial cables, for example, of the MRI system configured to receive MR data) may be wound, where the flat core forms a resonant circuit interacting with the cables. In one embodiment, as shown herein, the current trap 1502 is another example of a floating trap with a spiral core. However, whereas the floating trap of FIGS. 3-10 have a cylindrical spiral core, the current trap 1502 has a flat spiral core, e.g., configured to interface with the cables 1530 such that the cables are wound around the flat spiral core following a spiral, coiled path guided by a coiled wire, e.g., wire trace, of the current trap 1502.

A set of reference axes 1501 are provided, indicating an x-axis, a y-axis, and a z-axis. The current trap 1502 may generally lie in an x-y plane in accordance with the reference axes 1501, having a lateral width along the x-axis, a longitudinal length along the y-axis, and a height along the z-axis, which will be elaborated on herein. Further, the current trap 1502 may be a floating current trap, as previously discussed with relation to the current trap 302. The current trap 1502 may be implemented to provide high common mode impedance to mitigate adverse effects of common mode and/or shield currents. As such, the current trap 1502 may engage with transmission cables of an MRI system, as described herein, which may be subject to transmitter driven common mode currents which create field distortions and/or unpredictable heating of components.

The current trap 1502 may be formed having a flat core 1504 having a generally rectangular shape, in some examples. The flat core 1504 may include a frame 1506 and a printed circuit board (PCB) 1522 (e.g., carried, supported, and/or maintained in place by the frame 1506). Similar to the PCB 702 previously described, the PCB 1522 may include a variety of conductive tracks, pads and other features etched into laminated sheets of copper, which will be further described herein, particularly with respect to FIGS. 18-21. In one example, the frame 1506 may be formed of a nonconductive (e.g., insulating) material, such as plastic. As specifically illustrated in FIG. 15, the frame 1506 may have a width 1508 measured between first and second lateral sides 1510, 1512. Further, the frame may have a length 1514 measured between first and second longitudinal sides (or ends) 1516, 1518. Even further, the frame 1506 may have a height 1520 measured between a front and back (e.g., top and bottom sides) of the frame (e.g., along the z-axis). The width 1508 and the length 1514 are greater than the height 1520, as shown, such that the frame 1506 of the core 1504 has a flattened structure having the generally rectangular shape described above. For instance, in one example, the width 1508 and the length 1514 of the frame may be greater than 20 millimeters (mm), while the height 1520 may be less than 10 mm, in some examples. In this way, the core 1504 of the current trap 1502 may provide a stable structure of the current trap 1502, particularly suited for applications where space (e.g., height) is limited.

As illustrated in FIGS. 15-17, the PCB 1522 may be positioned within a central opening 1524 of the frame 1506 in the flat core 1504 of the current trap 1502. In some examples, the PCB 1522 may be attached to the frame 1506 by adhesive, for instance. In other examples, the PCB 1522 may be joined to the frame 1506 by other means, such as mechanical attachment devices. Further, in one example, the frame 1506 may be formed in multiple parts, as illustrated by first and second frame portions 1506a, 1506b in FIG. 16, and the flat core 1504 may be assembled by positioning the multiple parts of the frame to surround at least a periphery of the PCB 1522 and subsequently coupling the parts of the frame to each other and/or to the PCB. In other examples, however, the frame 1506 may be formed as a single piece (e.g., via injection molding), and the central opening 1524 sized to receive the PCB 1522, such that the PCB may be seated (e.g., coupled) within the central opening in any manner described herein. For instance, in one particular example, the frame may be formed as a single unitary structure with the central opening sized, and in some cases shaped on at least one side of the frame (e.g., on the top side), so that the PCB may be seated therein. As such, dimensions of the central opening may be similar to dimensions of the PCB. Further, the frame may include one or more protrusions, such as protrusion 1507 shown in FIG. 15, disposed within the central opening and designed for coupling with (e.g., engaging) one or more corresponding locating apertures formed in the PCB 1522, such as the locating apertures 1820 formed in opposite corners of the PCB 1522, particularly illustrated in FIGS. 18-20, so that the PCB may be easily positioned and mounted within the frame.

An exemplary structure of the PCB 1522, as well as the resonance circuitry formed by the PCB, will now be described with reference to FIGS. 18-21. A set of reference axes 1801 are provided in FIGS. 18-21, as well as FIG. 22, including an x-axis, a y-axis and a z-axis. The PCB 1522 may include three layers, each having conductive tracks (e.g., copper traces) formed thereon. More specifically, the PCB 1522 includes a top layer 1800 shown in FIG. 18, a middle layer 1900 shown in FIG. 19, and a bottom layer 2000 shown in FIG. 20. FIG. 21 shows a portion of the circuit 2100 formed by the layers of the PCB 1522, particularly illustrating electrical (e.g., conductive) connections formed between the layers. Each of the layers 1800, 1900, and 2000 may be a layer of copper with one or more laminated, non-conductive substrates (e.g., sheets or boards) 1802, positioned in between the layers. The substrates may have a similar rectangular shape (e.g., generally corresponding to the size of the central opening 1524 in the frame 1506 of the core 1504) and may be formed of a composite material, such as FR4, in one example. In other examples, the substrates may be formed of a material with a high dielectric constant and a low loss tangent. Further, the substrates may be stacked and joined together so as to form the PCB 1522 having a first end 1810 and a second end 1812, with a first side 1814 and a second side 1816 extending between the first and second ends. The first and second ends 1810, 1812 and the first and second sides 1814, 1816 of the PCB 1522 are indicated in each of FIGS. 18-21, for reference.

Turning now to FIG. 18, the substrate 1802 under the top layer 1800 of the PCB is shown to include a plurality of copper traces 1804 formed thereon or, alternatively, formed therein (e.g., between sheet layers of the substrate 1802). The copper traces 1804 may extend laterally, e.g., along the x-axis, across the top layer 1800. In one example, at least a portion of the copper traces 1804 extend between the first and second sides 1814, 1816 of substrate 1802. Further, a copper trace may be included near the first end 1810 and near the second end 1812. These particular copper traces 1804, near the first and second ends of the substrate 1802, may terminate in conductive pads to which one or more tuning capacitors 1808 may be coupled. In some examples, the tuning capacitors 1808 may be coupled to the top layer 1800 by soldering, for instance, to electrically connect the capacitors with the conductive traces 1804 on the substrate 1802 and mechanically couple the capacitors thereto. In one example, as illustrated in FIG. 18, two capacitors 1808 may be coupled to the substrate 1802, closer to the first end 1810 than the second end 1812 of the PCB 1522, and another capacitor 1808 may be coupled to the substrate 1802 closer to the second end 1812 than the first end 1810. In some examples, the capacitors nearer the first end 1810 of the PCB 1522 may be electrically connected in series, though these capacitors may be arranged in a parallel connection, in other examples.

The top layer 1800 of the PCB 1522 may further include sets of openings 1806 formed in the substrate 1802 and the copper traces 1804. In one example, the openings 1806 may be through holes (e.g., extending through the substrate and the copper traces) and may be made conductive via electroplating or may be lined with a conductive tube or rivet. In this way, the openings 1806 are designed for electrically connecting the conductive traces 1804 (and other components, such as the capacitors 1808 coupled thereto) with conductive traces formed in other layers, as will be elaborated on herein.

Similar to the top layer 1800 shown in FIG. 18, the substrate 1802 above the bottom layer 2000 of the PCB 1522, shown in FIG. 20, may be formed of a non-conductive material and may include a plurality of conductive copper traces 2004 formed on the substrate 1802 so as to extend between first and second sides 1814, 1816 of the PCB. The plurality of copper traces 2004 may extend laterally across the bottom layer 2000. The bottom layer 2000 may further include openings 2006 formed in the substrate 1802 and the copper traces 1804. Again, the openings 1806 may be through holes made conductive by electroplating or the inclusion of another conductive lining such as a tube or rivet.

Further, the middle layer 1900 shown in FIG. 19 may include another conductive track, illustrated as copper trace 1904. The copper trace 1904 may extend between the first and second ends 1810, 1812 of the PCB 1522. The middle layer may also include openings 1906 formed therein, extending through the substrate 1802 and the copper trace 1904, and also extending through the substrate in regions near the first and second sides 1814, 1816 (e.g., aligning with corresponding openings 1806 and 2006 formed in the top layer 1800 and the bottom layer 2000, respectively, of the PCB 1522 on first and second sides thereof). Further, the middle layer 1900 may additionally include sets of openings 1906 disposed at opposing ends of the copper trace 1904 (e.g., near the first and second axial ends 1814 and 1816, respectively).

When the copper layers and substrates are assembled, the locating apertures 1820 in opposing corners may be aligned so as to form the pair of locating apertures 1820 disposed at opposite corners of the PCB 1522, previously described for mating with protrusion(s) 1507 formed in the frame 1506 of FIG. 15 for mounting the PCB 1522 within the central opening thereof. To elaborate, the assembled PCB 1522 may include a first aperture at a corner between the first end 1810 and the second side 1816 of the PCB and a second aperture at a corner of the PCB between the second end 1812 and the first side 1814 of the PCB, in one example. Thus, in some examples, particularly when the frame 1506 (shown in FIGS. 15-17) is formed as a unitary structure, these locating apertures (e.g., the locating apertures 1820 shown in FIGS. 18-20, collectively) may be designed to couple to corresponding protrusions 1507 in an interference fit (e.g., press or snap fit) manner, for instance.

FIG. 21 illustrates a portion of the circuitry of the PCB 1522, particularly illustrating the electrical connections between the conductive tracks depicted in FIGS. 18-20 when the top, middle and bottom layers are assembled in the manner described above. More specifically, the copper traces 1804 and 2004 of the top and bottom layers 1800 and 2000, respectively, are shown, with the copper trace 1904 of the middle layer 1900 disposed therebetween. Also shown in FIG. 21 are conductive pads 2104 formed with some of the copper traces 1804 (in the top layer 1800) near first and second ends 1810 and 1812 of the PCB where the capacitors 1808 may be positioned (e.g., mechanically and electrically coupled).

The PCB 1522 further includes first sets of vias 2101 and second sets of vias 2102 for electrically coupling the conductive copper traces between the layers. For example, the openings 1806, 1906 and 2006 of the top, middle and bottom layers may align with one another (when the PCB is assembled), so that each of the vias in the first and second sets extends between a first opening in one of the layers to a second opening in another one of the layers that is aligned with the first opening. In this way, the copper traces formed in each layer may be electrically coupled by the vias to form a circuit, as desired. More specifically, the copper traces and the vias may be included in an outer portion of the resonant circuit of the current trap, forming a spiral or coiled conductive path, e.g., having a plurality of turns, that interfaces with one or more transmission cables. The copper trace 1904 of the middle layer 1900 of the PCB 1522 may be included in an inner portion of the resonant circuit. Together, the copper traces and the vias may form a continuous coiled wire, e.g., wire trace, forming a spiral path around the flat core of the current trap. It will be appreciated that reference to a wire described herein may refer to a free-standing wire that is not fixedly coupled to the spiral core of the current trap or any continuous conductive path formed by a plurality of conductive components, such as the wire trace described above.

In one particular example, for instance, the first vias 2101 may include a plurality of sets of three vias 2101 which extend between aligned copper traces 1804 and 2004, such that the sets of vias provide electrical coupling between corresponding sets of openings 1806 and 2006 located at opposite ends of the copper traces located near the opposing first and second sides 1814, 1816 of the PCB. However, it will be understood that the sets of vias and corresponding openings may have different numbers of vias/openings, in different examples. Further, a plurality of the copper traces 1804 and 2004 may be oriented on the respective substrates 1802, as shown oriented at angles 1805 and 2005 with respect to the x-axis in FIGS. 18 and 20, respectively, such that the resultant circuit formed by these copper traces and the vias includes a plurality of turns winding around the assembled PCB 1522 (e.g., across the top layer 1800 and the bottom layer 2000 in a direction generally between the first and second sides 1814 and 1816 of the PCB). The angles 1805 and 2005 may be substantially similar. The coupled copper traces 1804 and 2004 in the top and bottom layers of the PCB (specifically, the copper traces extending between first and second sides 1814, 1816 thereof in a region between the first and second ends 1810, 1812 thereof) therefore function as an inductor in the circuitry.

Further, as particularly illustrated in FIG. 21, the first vias 2102 may be positioned so as to electrically couple the copper trace 1904 of the middle layer 1900 with portions of certain ones of the copper traces 1804 of the top layer 1800. More specifically, in one example, the first sets of vias 2102 may include first and second sets of three vias 2102 extending between a corresponding set of three openings 1806 (shown in FIG. 18) in a copper trace 1804 and a set of three openings 1906 (shown in FIG. 19) in the copper trace 1904, at locations proximate the first and second ends 1810 and 1812 of the PCB, respectively. The circuit formed by the conductive copper traces and the vias is thus completed.

As previously described, the capacitors 1808 shown in FIGS. 15 and 18 may be electrically coupled with the circuitry depicted in FIG. 21 on conductive pads 2104 on the top layer 1800. The capacitors 1808 may be tuning capacitors carried by the PCB 1522 that form a resonance circuitry with the copper traces and vias formed through the layers of the PCB which function as an inductor in the circuitry, as described above. Therefore, contrary to the resonance circuitry in the exemplary current traps described with respect to FIGS. 3-10, the PCB 1522 formed in the manner described with respect to FIGS. 18-21 may provide resonance circuitry in an assembly such as the current trap 1502 shown in FIGS. 15-17 without the inclusion of a coiled wire wrapped around a spiral core. Further, a current trap utilizing the PCB 1522 to realize the desired resonance circuitry may have a more stable structure, with reduced complexity in the electrical couplings of the circuitry and assembly of the current trap, as will be further discussed with reference to FIGS. 15-17.

Turning again to FIGS. 15-17, where the PCB 1522 is assembled in the current trap 1502 within the central opening 1524 of the frame 1506 to form the flat core 1504, the structure of the frame 1506 will be elaborated on in the following description, particularly the structures which allow for the one or more cables 1530 to be wrapped around the flat core 1504 and retained by the frame 1506. The frame 1506 may include a plurality of ribs 1526 formed on each of the first and second lateral sides 1510, 1512. The ribs 1526 form slots 1528 in the fame 1506 extending between the top and bottom sides thereof (e.g., along the entire height 1520 of the frame). The slots 1528 are configured to receive individual turns of the wound cable(s) 1530, so that each turn of the one or more cables is spaced away from adjacent turns by the ribs 1526, which may therefore electrically insulate each turn. Further, the ribs 1526 on each of the lateral sides 1510, 1512 of the frame 1506 may be longitudinally offset from one another (e.g., along the y-axis, such that the turns of the one or more cables 1530 follow along a flattened spiraling path having a pitch 1527, as specifically illustrated in FIG. 16, defined by the ribs 1526.

In one example, the pitch 1527 (e.g., the distance between adjacent ribs 1526) may be equal to or greater than a sum of a diameter of a cable 1530 of the one or more cables plus a diameter of each additional cable to be positioned beside another cable (e.g., in the x-y plane, side-by-side in the direction of the y-axis) on the frame 1506 of the current trap 1502. In other examples, particularly when the one or more cable(s) have a flattened structure, the pitch 1527 may be equal to or greater than a sum of a width of a cable 1530 of the one or more cables plus a width of each additional cable to be positioned beside another cable (e.g., in the x-y plane, side-by-side in the direction of the y-axis). In other examples, the dimensions of the slots 1528 between the ribs 1526 may be configured to accommodate cable diameters (or widths) that differ from the diameter (or width) of another cable, where the slots are designed to maintain a position of the cables 1530 when they are wrapped around the flat core 1504.

For example, as illustrated in FIGS. 15-17, the one or more cables 1530 may be micro coaxial cables comprising three individual cables positioned side-by-side in the x-y plane. The pitch 1527 may therefore be equal to or greater than the sum of the diameter (or width) of each of the three cables 1530. Therefore, the cables 1530 may be received in each slot 1528 formed on the lateral sides 1510, 1512 of the frame 1506 as the cables are wrapped around the frame 1506 of the current trap 1502, such that the cables are positioned across the PCB 1522. Further, the pitch 1527 may be selected such that each turn of the cables 1530 extends across the frame 1506, and thus across the PCB 1522, at an angle relative to the x-axis. This angle may be substantially equal to the angle 1805 and/or the angle 2005 shown in FIGS. 19 and 20 (e.g., corresponding to the orientation of copper traces along the PCB), such that the cables 1530 follow along the copper traces 1804 and 2004 formed in the top and bottom layers 1800 and 2000 of the PCB 1522, as partially illustrated in FIG. 15.

In this way, with the cables 1530 wound along a path substantially adjacent the path formed by conductive copper traces in the PCB 1522, the cables 1530 are coupled to the aforementioned inductor formed by the copper traces of the PCB 1522 via electromagnetic induction. Further, as previously described, the inductor formed by the PCB 1522 and the tuning capacitors 1808 form a resonant circuit, whereby the resonant circuit has a high impedance to shield currents generated in shields of the cables 1530 and can reduce shield currents through the electromagnetic coupling with the cables 1530. To elaborate, the inductor formed by the PCB 1522 (e.g., by the layout and coupling of copper traces in layers of the PCB) enables the current trap 1502 to interact with the cables 1530 through electromagnetic induction, creating an electromagnetic field when a shield current flows through the cables, which impedes the shield current via the resonant circuit of the current trap 1502. In some examples, the proximity of the cables 1530 to the resonant circuit provided by the design of the core 1504 and the layout of the PCB 1522 may allow for stronger electromagnetic coupling between the cables and the resonant circuit, when compared to previous current trap designs, thereby enhancing performance of the current trap 1502. Further, such a current trap may not require a coiled wire to form the resonant circuit, instead using a single PCB 1522 with tuning capacitors carried thereon to form the resonant circuit, thereby reducing costs and complexities associated with manufacturing and assembly of the current trap 1502.

Even further, the compact, flattened structure of the frame 1506 and PCB 1522 of the flat core 1504 provides a stable, sturdy structure to which the one or more cables 1530 can be readily and quickly coupled (e.g., wound around at a desired position along the cable(s) 1530), which may also function to protect the integrity of the resonant circuit formed by the current trap 1502. Further, the current trap 1502 may be tuned by coupling a probe to the PCB 1522 to adjust the impedance to block a target frequency, such as 127.7 MHz, before the current trap 1502 is coupled to a cable. In other words, the current trap 1502 may be pre-tuned during manufacturing and provided as a tuned, ready-to-use device offering sufficient impedance to shield currents generated in the cables wrapped around the flat core 1504. In some examples, the flattened, more planar design of the current trap 1502 may offer lower inductance compared to the generally cylindrical current trap 302 shown in FIGS. 3-9. However, the current trap 1502 may be particularly desirable in situations where space or height is limited, whereby impedance may be effectively increased as desired for a given application by increasing the size of the current trap 1502.

Therefore, equipping the MRI system with at least one floating current trap 1502 may mitigate or circumvent issues that may arise with the generation of shield currents on the cables 1530, which may include localized heating of the cables, distortion of MRI system images, and adverse effects on tuning. Further, the resonant circuit formed by the PCB 1522 and the tuning capacitors 1808 allows the current trap 1502 to be tuned away from and independent of the MRI system (e.g., during manufacturing), as explained above, such that use of the current trap 1502 may be expedited by precluding the time-consuming tuning procedure. The tuning capacitors 1808 may be adjusted to provide an impedance of the current trap 1502 that blocks a resonant frequency of a shield current carried by the cables 1530. However, in other examples, the current trap 1502 may be configured to block a range of frequencies to enable the current trap 1502 to be used across a variety of systems with varying resonance frequencies to be impeded.

In some examples, referring collectively to FIGS. 15-17, the cables 1530 may be wound around the frame 1506 and the PCB 1522 of the flat core 1504 such that a first portion 1542 of the cables 1530 is received and retained in one or more first openings or slots, such as an opening 1538 formed in the frame 1506. The opening 1538 may be formed on the first lateral side 1510 of the frame 1506 closer to the first longitudinal end 1516 of the frame than the second longitudinal end 1518 (e.g., proximate a first corner defined between the first lateral side 1510 and the first longitudinal end 1516). A second portion 1544 of the cables 1530, at a different position from the first portion 1542 along a length of the cables, may be similarly received and retained in one or more second openings or slots, such as an opening 1540 formed on the second lateral side 1512 of the frame 1506, closer to the second longitudinal end 1518 of the frame than the first longitudinal end 1516 (e.g., proximate a second corner defined between the second lateral side 1512 and the second longitudinal end 1518, opposite the first corner). In some examples, the openings 1538, 1540 may be included in extensions of the frame 1506 that protrude laterally outward from the first and second lateral sides 1510, 1512, respectively. Even further, as particularly illustrated in FIG. 17, the first and second openings 1538, 1540 may not circumferentially surround or substantially enclose the respective first and second ends of the cables 1530. Rather, the openings 1538, 1540 may be configured as sleeves that surround only a portion of a periphery of the cables 1530.

A third portion of the cables 1530 defined between the first portion 1542 and 1544 is therefore wrapped around the flat core 1504, following the path of copper traces in the PCB 1522, as previously described, with each of the turns of the cables 1530 retained in the slots 1528. In FIGS. 15-17, the cables 1530 may each have four turns, corresponding to four slots 1528 formed on each of the lateral sides 1510, 1512 of the frame 1506. However, other numbers of turns of the cables 1530 and therefore the slots 1528 between the ribs 1526 have been contemplated, such as 3, 5, 6, 7, 8, etc., in different examples. In these other examples, the PCB 1522 may also be modified to include more or less copper traces formed in top and bottom layers thereof so as to correspond to the path of the turns of the cables 1530. Further, in some examples, as illustrated in FIGS. 15-17, the cables 1530 may include three cables arranged side-by-side so as to substantially fill each of the slots 1528 in the frame 1506. However, in other examples, one of which will be elaborated on herein with respect to FIG. 22, the cables 1530 may include two cables or four cables which may be arranged in a side-by-side configuration in the x-y plane and/or stacked in the direction of the z-axis.

It will be understood that the current trap 1502, along with any of the floating current traps described herein, may be reconfigured along the at least one cable 1530 in a similar manner to that of the current trap 1302, depicted in FIG. 13. Thus, the current trap 1502 may be coupled to cables 1530 extending between a processing unit and a receive coil of an MRI system at a first location along the cables by wrapping the cables around the flat core 1504 in the above-described configuration. The current trap 1502 may then be relocated along the cables to a second location by unwinding the cables 1530 from the flat spiral core 1504 and moving the current trap 1502 along the cables to a second location different from the first location. In this way, the current trap 1502 may be readily positioned and re-positioned at any point along the cables 1530, as desired, without cutting or soldering of the cables, mitigating potential damage and exposure of the cables to high temperatures.

FIG. 22 shows a perspective view 2200 of another current trap 2202 according to another exemplary embodiment of the disclosure. A set of reference axes 2201 are provided, indicating an x-axis, a y-axis and a z-axis. The current trap 2202 may be substantially similar to the current trap 1502 shown in FIGS. 15-17, and may therefore include a flat core 2204 including a frame 2206 surrounding a PCB (with tuning capacitors) mounted within a central opening of the frame, such as the PCB 1522 described with respect to FIGS. 15-21. The current trap 2202 is configured with one or more cables 2230 wrapped around the core, each turn of the cables held within one of a plurality of slots 2228 defined between ribs 2226 of the frame, as partially shown in FIG. 22. Similar to the flat core 1504 shown in FIGS. 15-17, the frame 2206 may be generally rectangular and formed as a multi-piece or a unitary structure, and the slots 2228 may be formed on each of opposing lateral sides 2210, 2212 of the frame 2206 which extend between a first longitudinal end 2214 and a second longitudinal end 2216 of the frame. Due to the above-mentioned similarities, repeat discussion of the frame and the PCB of the flat core 2204, as well as the manner in which the cables 2230 are wrapped around the core and electromagnetically coupled with a resonant circuit formed by the PCB and tuning capacitors carried by the PCB, will be omitted for brevity.

The flat core 2204 of the current trap 2202 shown in FIG. 22 may further include a cover 2240 positioned on a top side 2242 of the frame 2206 and/or a second cover 2244 positioned on a bottom side 2246 of the frame. The covers 2240, 2244 may have a generally rectangular shape, substantially the same as the shape of the frame 2206 (e.g., having a similar width, as measured between lateral sides 2210, 2212, and a similar length, as measured between longitudinal ends 2214, 2216), so that the covers may extend across the PCB positioned within the frame. Further, in one example, the covers 2240, 2244 may be removably coupled to the frame 2206 by suitable mechanical fasteners, which may allow the current trap 2202 to be more easily repositioned along a length of the cables 2230, as desired. In other examples, however, the covers may be coupled to the frame by other suitable means, such as an adhesive, for instance. Even further, the covers 2240, 2444 may be made of an insulating non-conductive material, such as plastic.

In some examples, the current trap 2202 may further include a shield 2250 positioned about an exterior of the flat core 2204, as indicated via dashed lines. The shield 2250 may be formed from an electromagnetically insulating material. For example, the shield 2250 may be a relatively thin copper tape that may be wrapped around the core 2204 and the covers 2240, 2244. Specifically, the copper tape may extend across the frame 2206 on the first longitudinal end 2214 thereof, the bottom (e.g., exterior) surface of the cover 2244, the second longitudinal end 2216 of the frame 2206, and the top (e.g., exterior) surface of the cover 2240. In this way, the shield 2250 may not cover the first and second lateral sides 2210, 2212 of the frame 2206, so as to avoid interfering with the placement of turns of the cables 2230 around the core 2204 (e.g., in the slots 2228 between the ribs 2226), as illustrated. Further, when the shield 2250 is formed as a strip of copper tape, one side of the shield may include an adhesive for joining the shield to the longitudinal ends of the frame and the exterior surfaces of the covers. Even further, in some examples, upon wrapping the copper tape of the shield 2250 about the current trap, two opposing end portions of the tape may be joined together at a seam 2252, for instance, by soldering, though other suitable attachment means have been contemplated, in different examples. The shield 2250 may reduce electromagnetic radiation generated by the current trap 2202 which may reduce a likelihood of undesirable electromagnetic coupling between the current trap and coil elements of an MRI system.

FIG. 22 also depicts an alternative example of openings in the frame 2206 for receiving first and second end portions of the cables 2230. For example, the frame 2206 may include one or more slots 2238 formed on the lateral side 2210, closer to the first longitudinal end 2214 than the second longitudinal end 2216, for receiving and retaining the one or more cables 2230. The one or more slot(s) may be designed so as to open to one of the top or bottom sides of the frame. In one example, the one or more slots 2238 may include two slots located on the lateral side 2210 of the frame and opening to the bottom side 2246 of the frame. Further, the slots 2238 may each may be shaped and sized so as to snugly retain a cable 2230 positioned therein, so that the cables may be suitably and reliably positioned (e.g., oriented in the first lateral side 2210 of the frame) for being wrapped about the core 2204 of the current trap 2202. In other examples, the one or more cables 2230 may comprise more than two cables. For instance, when one or three cables are wrapped around the core 2204 of the current trap, one or three slots 2238 may be distinctly formed in the frame for retaining each of the cables.

Further, in one particular example, as illustrated in FIG. 22, the one or more cables 2230 may comprise four cables. Accordingly, the frame 2206 may include two slots 2238 formed on the first lateral side 2210 thereof (in the configuration described above) for retaining a first pair of cables 2230 of the four cables. Upon winding the first pair of cables 2230 about the core 2204, a second pair of cables 2230 of the four cables may be wound about the core, such that the second pair of cables is adjacent the first pair of cables (e.g., stacked in the direction of the z-axis), and the first and second pairs of cables follow substantially the same path around the frame 2206 and across the PCB mounted therein. As depicted, the cover 2244 coupled to the bottom side 2246 of the frame 2206 may further assist in retaining and maintaining the position of the cables 2230, by blocking the portion of the one or more slots 2238 that opens to the bottom side of the frame. Although not particularly shown in FIG. 22, the frame 2206 may further include one or more additional openings or slots formed in the second lateral side 2212 of the frame, closer to the second longitudinal end 2216 than the first longitudinal end 2214 of the frame, for retaining a second portion of the one or more cables 2230 wound about the core 2204. These additional opening(s) or slot(s) may be substantially the same as the slot(s) 2238, opening to the bottom side of the frame, in some examples, such that the bottom cover 2244 again assists in retaining the cables in the current trap.

FIG. 11 is a high-level block diagram illustrating an example method 1100 for blocking transmission-induced (e.g., shield) currents at shields of or one or more transmission cables, e.g., a coaxial cable bundle, by coupling the transmission cables to a device for impeding the shield currents, such as the floating trap assembly 703 of FIGS. 7 and 8, the current trap 1502 of FIGS. 15-17, or the current trap 2202 of FIG. 22, according to various embodiment of the disclosure. The floating trap assembly and current traps are collectively referred to as a balun assembly hereafter. Prior to engagement with the transmission cables, the device may be tuned to a resonance frequency that is equal or close to an operating frequency of an MRI system via tuning capacitors coupled to a PCB of the device. The transmission cables may be successively wrapped around the floating trap assembly, as previously described.

Method 1100 begins at 1102. At 1102, RF energy generated at a body coil of the MRI system is transmitted to the transmission cables. The signal transmission generates a shield current which is carried along the shields of the transmission cables at 1104. At 1106, the balun assembly traps the RF current at the transmission cables. For example, a high impedance of the balun assembly, where the resonant frequency is pre-set (e.g., tuned) to the operating frequency of the MRI system, reduces the shield current.

The technical effect of the disclosure may include improved performance of MRI systems due to reduced interaction between transmission cables and coil elements. Another technical effect of the disclosure may include achieving desired impedance of a balun assembly via a single balun, e.g., a single floating trap or single current trap. Yet another technical effect of the disclosure may include positioning the balun assembly anywhere along the transmission cables. Yet another technical effect of the disclosure may include reducing a coil surface temperature relative to a feed board of an MRI system.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

The invention will be further described in the following paragraphs. In one aspect, a current trap is provided that comprises a flat core including a nonconductive material; a coiled wire having a plurality of turns wound around the flat core; and one or more tuning capacitors physically attached to the flat core and electrically connected to the coiled wire to form a resonant circuit with the coiled wire.

In another aspect, a floating current trap assembly is provided that comprises a current trap comprising a flat core including a frame formed of a nonconductive material; a coiled wire having a plurality of turns wound around the flat core; and one or more tuning capacitors electrically connected to the coiled wire to form a resonant circuit with the coiled wire; and one or more cables wound around the flat core and stacked on the coiled wire, wherein the resonant circuit has a high impedance for common mode currents carried by the one or more cables.

In yet another aspect, a radio frequency (RF) coil unit for magnetic resonance imaging (MRI) is provided, the RF coil unit comprising one or more RF coil elements; a transmission cable electrically coupled to the one or more RF coil elements; and a current trap comprising a flat core including a printed circuit board (PCB) attached to a frame formed of a nonconductive material; a coiled wire having a plurality of turns wound around the flat core; and one or more tuning capacitors carried by the PCB and electrically connected to the coiled wire to form a resonant circuit with the coiled wire, wherein the transmission cable is wound around the flat core and stacked on the coiled wire.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. A current trap comprising:
a flat core including a nonconductive material;
a coiled wire having a plurality of turns wound around the flat core; and
one or more tuning capacitors physically attached to the flat core and electrically connected to the coiled wire to form a resonant circuit with the coiled wire.

2. The current trap of claim 1, wherein the flat core comprises a frame including a plurality of ribs on opposing sides, the plurality of ribs forming a plurality of spaces each for receiving one of the plurality of turns of one or cables wrapping around the flat core.

3. The current trap of claim 2, wherein the flat core further comprises a printed circuit board (PCB) mounted within the frame, wherein the one or more tuning capacitors are carried by the PCB.

4. The current trap of claim 3, wherein a width of the frame is greater than a height of the frame.

5. The current of claim 3, wherein the PCB includes a plurality of conductive traces forming the coiled wire, the plurality of conductive traces including a first set of conductive traces extending laterally across an upper surface of the flat core and a second set of conductive traces extending laterally across a bottom surface of the flat core.

6. The current trap of claim 5, wherein the first and second set of conductive traces extend laterally at an angle relative to a lateral axis of the flat core and form an outer portion of the resonant circuit, and wherein a single conductive trace forms an inner portion of the resonant circuit and extends between opposite ends of the PCB.

7. The current trap of claim 6, wherein the first set of conductive traces is coupled to the second set of conductive traces by a plurality of vias, and wherein the first set of conductive traces is spaced apart from the second set of conductive traces by the plurality of vias.

8. The current trap of claim 3, wherein the plurality of turns of the coiled wire are wound around opposing sides of the PCB.

9. A floating current trap assembly comprising:
a current trap comprising:
a flat core including a frame formed of a nonconductive material;
a coiled wire having a plurality of turns wound around the flat core; and
one or more tuning capacitors electrically connected to the coiled wire to form a resonant circuit with the coiled wire; and
one or more cables wound around the flat core and stacked on the coiled wire,
wherein the resonant circuit has a high impedance for common mode currents carried by the one or more cables.

10. The floating current trap assembly of claim 9, wherein the one or more cables are coupled to the coiled wire though electromagnetic coupling.

11. The floating current trap assembly of claim 9, wherein a position of the current trap relative to the one or more cables is reconfigurable by unwinding the one or more cables from the flat spiral core at a first position and rewinding the one or more cables on the flat core at a second position.

12. The floating current trap assembly of claim 9, wherein the flat spiral core further comprises a printed circuit board (PCB) attached to the frame, wherein the one or more tuning capacitors are carried by the PCB, and the frame comprises a plurality of slots on first and second sides thereof, each slot configured for receiving the one or more cables.

13. The floating current trap assembly of claim 12, wherein a first end of the one or more cables is retained in one or more first openings formed on a first lateral side of the frame closer to a first longitudinal end of the frame than a second longitudinal end of the frame, and a second end of the one or more cables is retained in one or more second openings formed on a second lateral side of the frame closer to the second longitudinal end of the frame than the first longitudinal end.

14. The floating current trap assembly of claim 12, wherein a first electrical connection end for the one or more tuning capacitors is formed on the PCB and is electrically connected to a first end of the coiled wire, and a second electrical connection end for the one or more tuning capacitors is formed on the PCB and is electrically connected to a second end of the coiled wire.

15. The floating current trap assembly of claim 12, wherein a width of the flat core is greater than a height of the flat core, wherein the frame includes at least one shield wrapped around outer surfaces of the frame.

16. The floating current trap assembly of claim 15, wherein the frame is made of plastic.

17. The floating current trap assembly of claim 12, wherein the PCB is fixed within a central opening of the frame.

18. A radio frequency (RF) coil unit for magnetic resonance imaging (MRI), the RF coil unit comprising:
- one or more RF coil elements;
- a transmission cable electrically coupled to the one or more RF coil elements; and
- a current trap comprising:
  - a flat core including a printed circuit board (PCB) attached to a frame formed of a nonconductive material;
  - a coiled wire having a plurality of turns wound around the flat core; and
  - one or more tuning capacitors carried by the PCB and electrically connected to the coiled wire to form a resonant circuit with the coiled wire,
- wherein the transmission cable is wound around the flat core and stacked on the coiled wire.

19. The RF coil unit of claim 18, wherein the transmission cable is coupled to the coiled wire through electromagnetic coupling, and wherein the resonant circuit provides a high impedance for a common mode current carried by the transmission cable.

20. The RF coil unit of claim 18, wherein a position of the current trap relative to the transmission cable is reconfigurable.

* * * * *